(12) United States Patent
Blomquist

(10) Patent No.: US 9,119,917 B2
(45) Date of Patent: Sep. 1, 2015

(54) SYSTEMS AND METHODS TO ADDRESS AIR, LEAKS AND OCCLUSIONS IN AN INSULIN PUMP SYSTEM

(71) Applicant: TANDEM DIABETES CARE, INC., San Diego, CA (US)

(72) Inventor: Michael Blomquist, Blaine, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 14/107,490

(22) Filed: Dec. 16, 2013

(65) Prior Publication Data

US 2014/0107609 A1    Apr. 17, 2014

Related U.S. Application Data

(63) Continuation of application No. 12/729,985, filed on Mar. 23, 2010, now Pat. No. 8,608,699.

(60) Provisional application No. 61/165,275, filed on Mar. 31, 2009.

(51) Int. Cl.
*A61M 5/168* (2006.01)
*A61M 5/142* (2006.01)
(Continued)

(52) U.S. Cl.
CPC ......... *A61M 5/16854* (2013.01); *A61M 5/1452* (2013.01); *A61M 5/14244* (2013.01); *A61M 5/16831* (2013.01); *G01M 3/26* (2013.01); *A61M 5/365* (2013.01); *A61M 2005/16872* (2013.01);
(Continued)

(58) Field of Classification Search
CPC ..................... A61M 5/16854; A61M 5/14244; A61M 5/16831; A61M 5/1452; G01M 3/26
USPC ........... 604/65–67, 131, 151; 128/DIG. 1, 12, 128/13
See application file for complete search history.

(56) References Cited

U.S. PATENT DOCUMENTS 4,634,426 A * 1/1987 Kamen ........................... 604/65
5,000,664 A   3/1991 Lawless et al.
(Continued)

FOREIGN PATENT DOCUMENTS

DE           4013769       10/1991
WO         WO0045696        8/2000
(Continued)

OTHER PUBLICATIONS

Written Opinion and International Search Report for International Application No. PCT/US2010/029339 dated Aug. 4, 2010.
(Continued)

*Primary Examiner* — Manuel Mendez
(74) *Attorney, Agent, or Firm* — Patterson Thuente Pedersen, P.A.

(57) ABSTRACT

A system and method for adjusting insulin infusion volume based on air in an infusion set tube includes inputting at least one location and length of an air bubble along the infusion set tube. An air bubble volume is determined in the infusion set tube. An insulin infusion volume is determined based on a desired insulin infusion. A determination is then made whether the desired insulin infusion would include the air bubble volume based on the inputted location and length of the air bubble. The air bubble volume is added to the insulin infusion volume to make an adjusted insulin infusion volume if the insulin infusion volume includes the air bubble.

17 Claims, 21 Drawing Sheets

(51) Int. Cl.
*A61M 5/145* (2006.01)
*G01M 3/26* (2006.01)
*A61M 5/36* (2006.01)

(52) U.S. Cl.
CPC ........ *A61M 2205/15* (2013.01); *A61M 2205/18* (2013.01); *A61M 2205/3331* (2013.01)

(56) References Cited

U.S. PATENT DOCUMENTS

| | | | |
|---|---|---|---|
| 5,049,141 A | 9/1991 | Olive |
| 5,059,171 A | 10/1991 | Bridge et al. |
| 5,064,412 A | 11/1991 | Henke et al. |
| 5,181,910 A | 1/1993 | Scanlon |
| 5,190,522 A | 3/1993 | Wojcicki et al. |
| 5,338,157 A | 8/1994 | Blomquist |
| 5,368,562 A | 11/1994 | Blomquist et al. |
| 5,389,078 A | 2/1995 | Zalesky et al. |
| 5,392,638 A | 2/1995 | Kawahara |
| 5,485,408 A | 1/1996 | Blomquist |
| 5,505,777 A | 4/1996 | Ciardella et al. |
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,695,473 A | 12/1997 | Olsen |
| 5,711,989 A | 1/1998 | Ciardella et al. |
| 5,800,387 A | 9/1998 | Duffy et al. |
| 5,810,771 A | 9/1998 | Blomquist |
| 5,879,143 A | 3/1999 | Cote et al. |
| 5,935,099 A | 8/1999 | Peterson et al. |
| 5,935,106 A | 8/1999 | Olsen |
| 5,964,724 A | 10/1999 | Rivera et al. |
| 6,024,539 A | 2/2000 | Blomquist |
| 6,077,055 A | 6/2000 | Vilks |
| 6,164,924 A | 12/2000 | Gruett et al. |
| 6,241,704 B1 | 6/2001 | Peterson et al. |
| 6,248,067 B1 | 6/2001 | Causey, III et al. |
| 6,280,408 B1 | 8/2001 | Sipin |
| 6,422,057 B1 | 7/2002 | Anderson |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,641,533 B2 | 11/2003 | Causey, III et al. |
| 6,652,493 B1 | 11/2003 | Das |
| 6,744,350 B2 | 6/2004 | Blomquist |
| 6,749,587 B2 | 6/2004 | Flaherty |
| 6,809,653 B1 | 10/2004 | Mann et al. |
| 6,830,558 B2 | 12/2004 | Flaherty et al. |
| 6,852,104 B2 | 2/2005 | Blomquist |
| 6,872,200 B2 | 3/2005 | Mann et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,098,803 B2 | 8/2006 | Mann et al. |
| 7,109,878 B2 | 9/2006 | Mann et al. |
| 7,189,352 B2 | 3/2007 | Carpenter et al. |
| 7,198,751 B2 | 4/2007 | Carpenter et al. |
| 7,204,958 B2 | 4/2007 | Olsen et al. |
| 7,324,012 B2 | 1/2008 | Mann et al. |
| 7,357,899 B2 | 4/2008 | Gaillard et al. |
| 7,682,563 B2 | 3/2010 | Carpenter et al. |
| 7,687,272 B1 | 3/2010 | Buchwald et al. |
| 7,951,112 B2 | 5/2011 | Patzer |
| 7,959,715 B2 | 6/2011 | Kavazov et al. |
| 7,963,954 B2 | 6/2011 | Kavazov |
| 7,972,296 B2 | 7/2011 | Braig et al. |
| 8,313,308 B2 | 11/2012 | Lawless et al. |
| 8,361,021 B2 | 1/2013 | Wang et al. |
| 8,409,142 B2 * | 4/2013 | Causey et al. ................. 604/151 |
| 8,414,563 B2 | 4/2013 | Kamen et al. |
| 8,449,524 B2 | 5/2013 | Braig et al. |
| 8,608,699 B2 | 12/2013 | Blomquist |
| 2001/0031944 A1 | 10/2001 | Peterson et al. |
| 2002/0183693 A1 | 12/2002 | Peterson et al. |
| 2003/0212364 A1 | 11/2003 | Mann et al. |
| 2004/0073095 A1 | 4/2004 | Causey, III et al. |
| 2004/0204673 A1 | 10/2004 | Flaherty |
| 2005/0030164 A1 | 2/2005 | Blomquist |
| 2005/0124929 A1 | 6/2005 | Katz et al. |
| 2005/0171513 A1 | 8/2005 | Mann et al. |
| 2005/0214129 A1 | 9/2005 | Greene et al. |
| 2006/0001550 A1 | 1/2006 | Mann et al. |
| 2006/0132292 A1 | 6/2006 | Blomquist |
| 2006/0140798 A1 | 6/2006 | Kutsuzawa |
| 2006/0202859 A1 | 9/2006 | Mastrototaro et al. |
| 2007/0156033 A1 | 7/2007 | Causey, III et al. |
| 2007/0185429 A1 | 8/2007 | O'Mahony et al. |
| 2008/0030369 A1 | 2/2008 | Mann et al. |
| 2008/0033357 A1 | 2/2008 | Mann et al. |
| 2008/0103445 A1 | 5/2008 | Blaine et al. |
| 2008/0267599 A1 | 10/2008 | Arnold et al. |
| 2008/0269680 A1 | 10/2008 | Ibranyan et al. |
| 2008/0269681 A1 | 10/2008 | Kavazov et al. |
| 2008/0269682 A1 | 10/2008 | Kavazov et al. |
| 2008/0287887 A1 | 11/2008 | Mack et al. |
| 2009/0270833 A1 | 10/2009 | Debelser et al. |
| 2009/0275887 A1 * | 11/2009 | Estes ........................... 604/67 |
| 2009/0292245 A1 | 11/2009 | Basso et al. |
| 2010/0185142 A1 | 7/2010 | Kamen et al. |
| 2010/0185175 A1 | 7/2010 | Kamen et al. |
| 2010/0198183 A1 | 8/2010 | Lanigan et al. |
| 2010/0256466 A1 | 10/2010 | Shekalim et al. |
| 2010/0262078 A1 | 10/2010 | Blomquist |
| 2011/0071465 A1 | 3/2011 | Wang et al. |
| 2011/0092894 A1 | 4/2011 | Mcgill et al. |
| 2011/0125085 A1 | 5/2011 | Mcgill et al. |
| 2011/0190694 A1 | 8/2011 | Lanier, Jr. et al. |
| 2011/0190700 A1 | 8/2011 | Kavazov et al. |

FOREIGN PATENT DOCUMENTS

| | | |
|---|---|---|
| WO | WO0152727 | 7/2001 |
| WO | WO2007122621 | 11/2007 |
| WO | WO2009026420 | 2/2009 |

OTHER PUBLICATIONS

IPRP for International Application No. PCT/US2010/029339 dated Oct. 13, 2011.
Chinese Office Action for Chinese Application No. 201080023991.5 dated Jun. 18, 2013. English Translation provided.
Japanese Office Action for Japanese Application No. 2012053648 issued on Feb. 4, 2014. English Translation Provided.
Application and File History for U.S. Appl. No. 12/729,985 filed Mar. 23, 2010, inventor Blomquist.
European Search Report for European Application No. EP10762209 dated May 8, 2014.
Office Action dated Dec. 17, 2014 for Australian Patent Application No. 2010234736 filed Mar. 31, 2010, 4 pages.

* cited by examiner

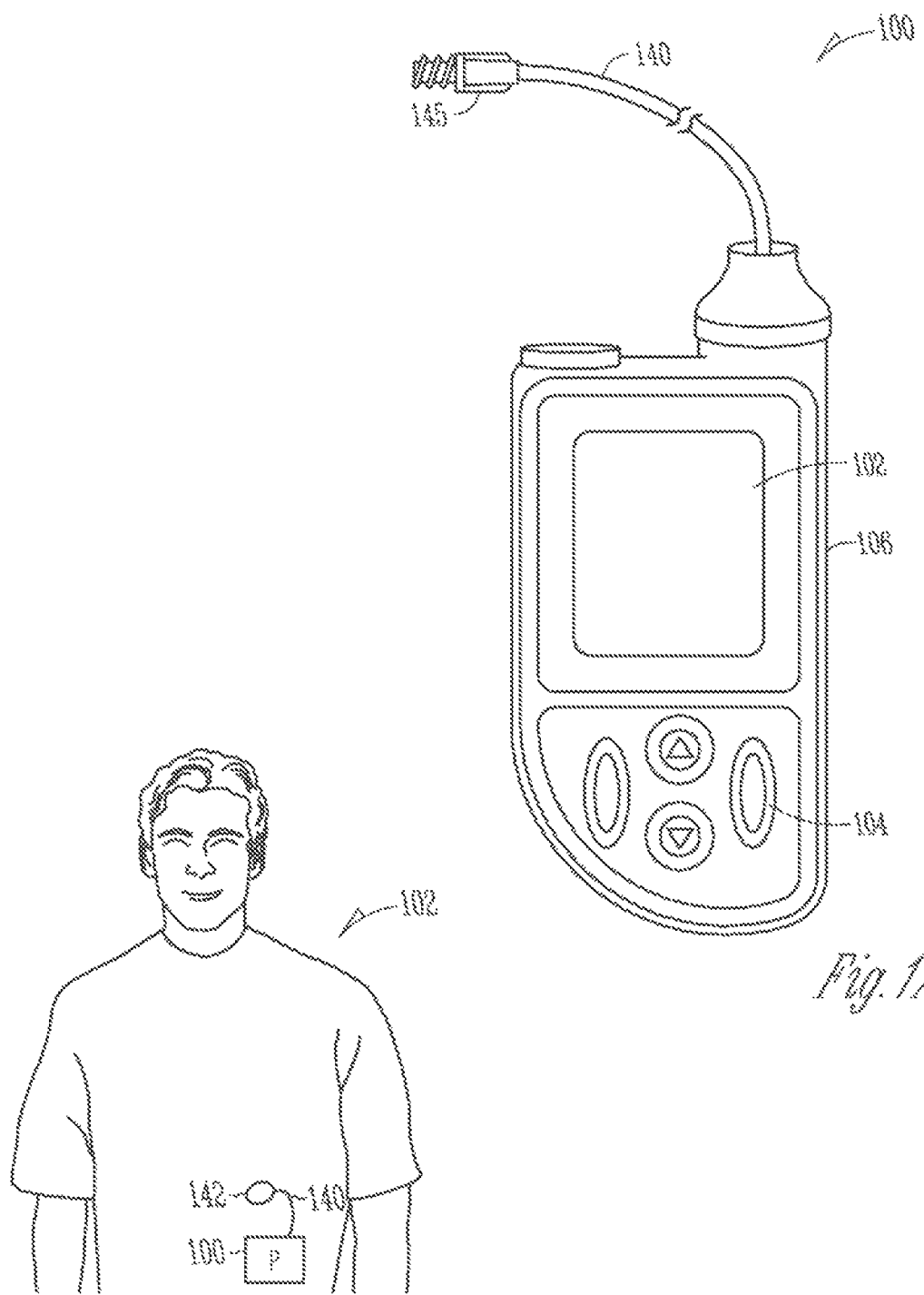

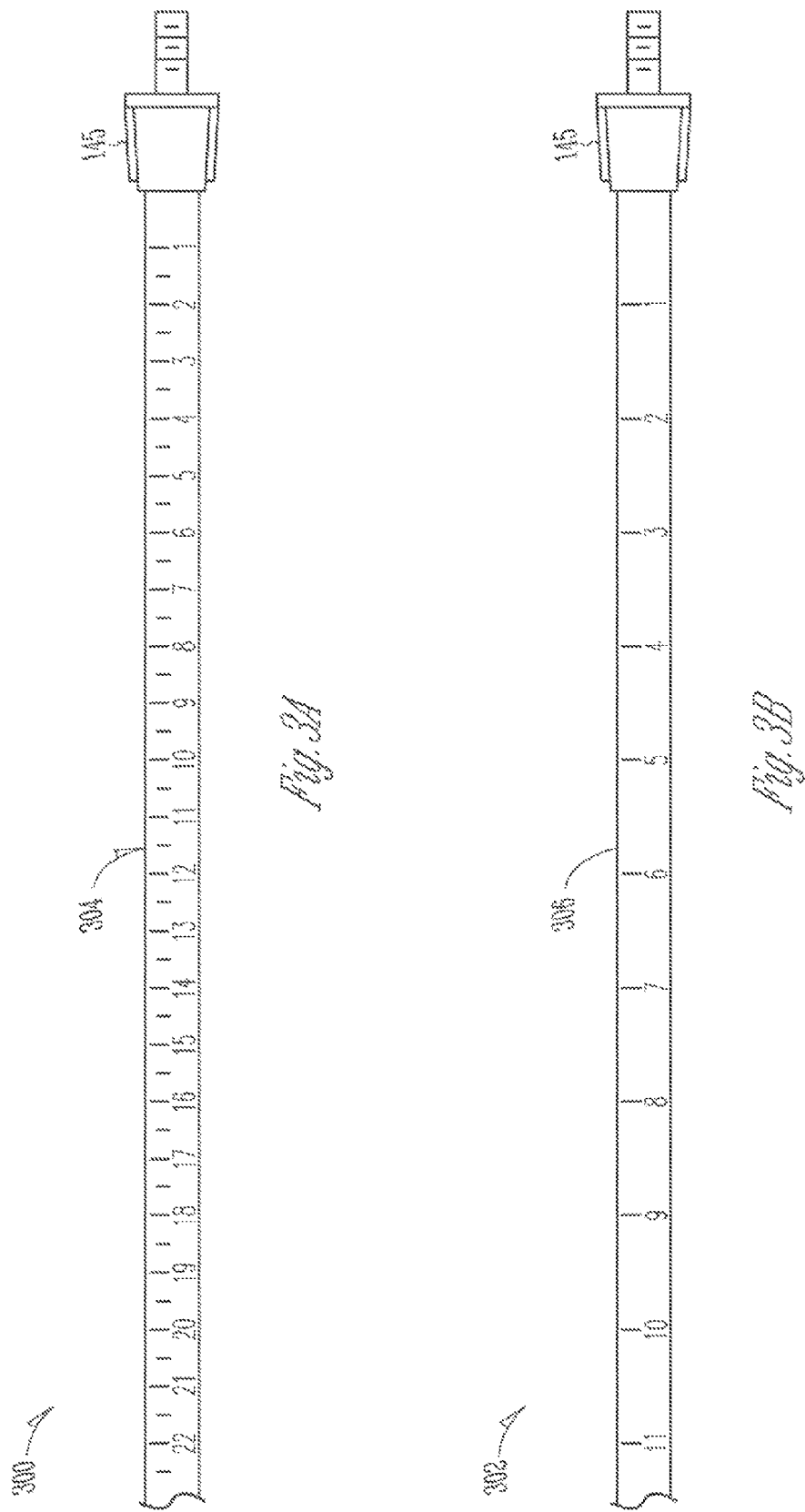

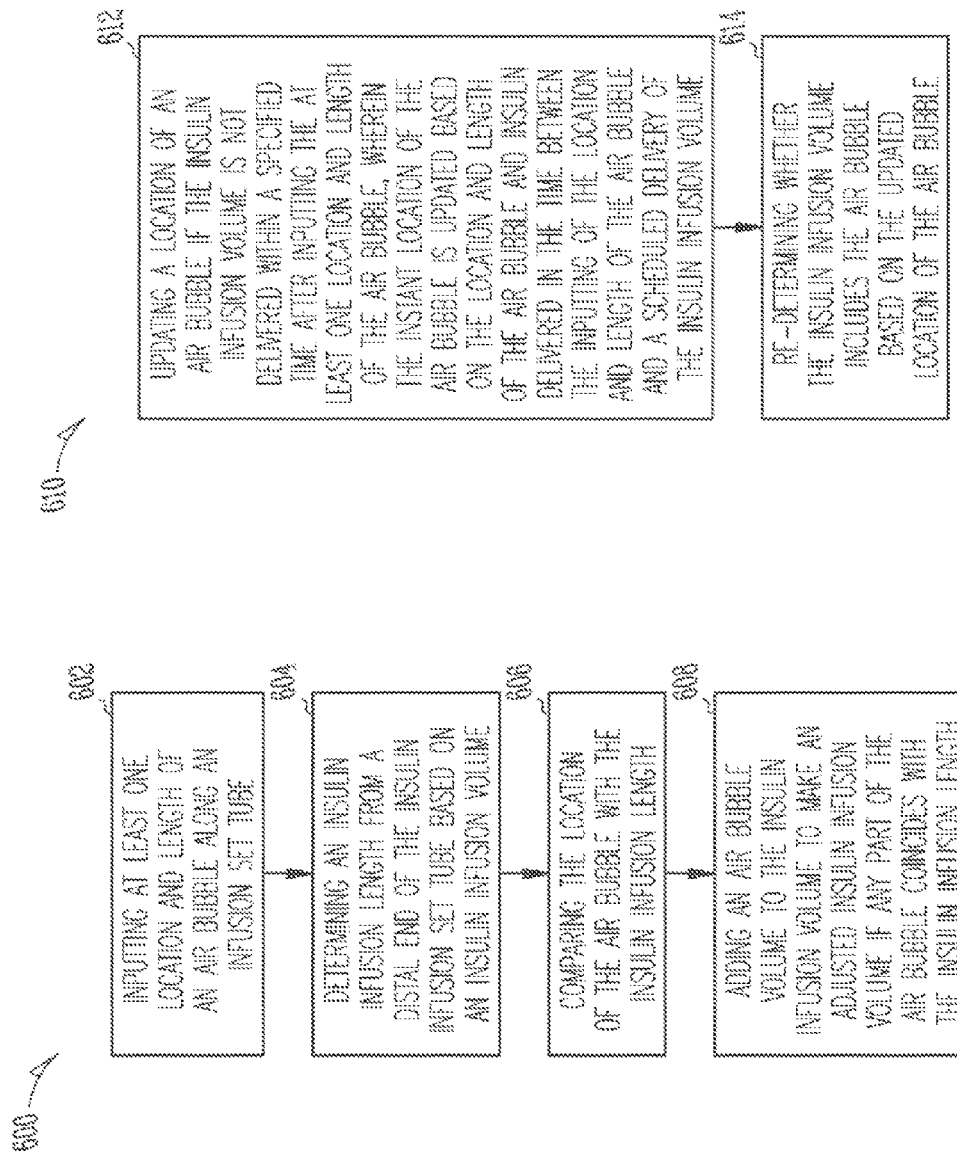

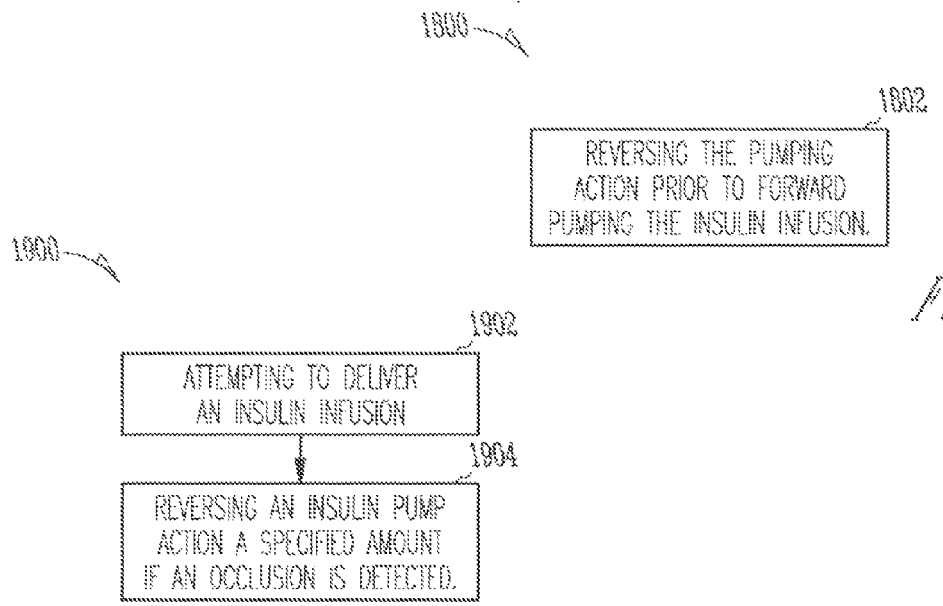
Fig. 18
Fig. 19
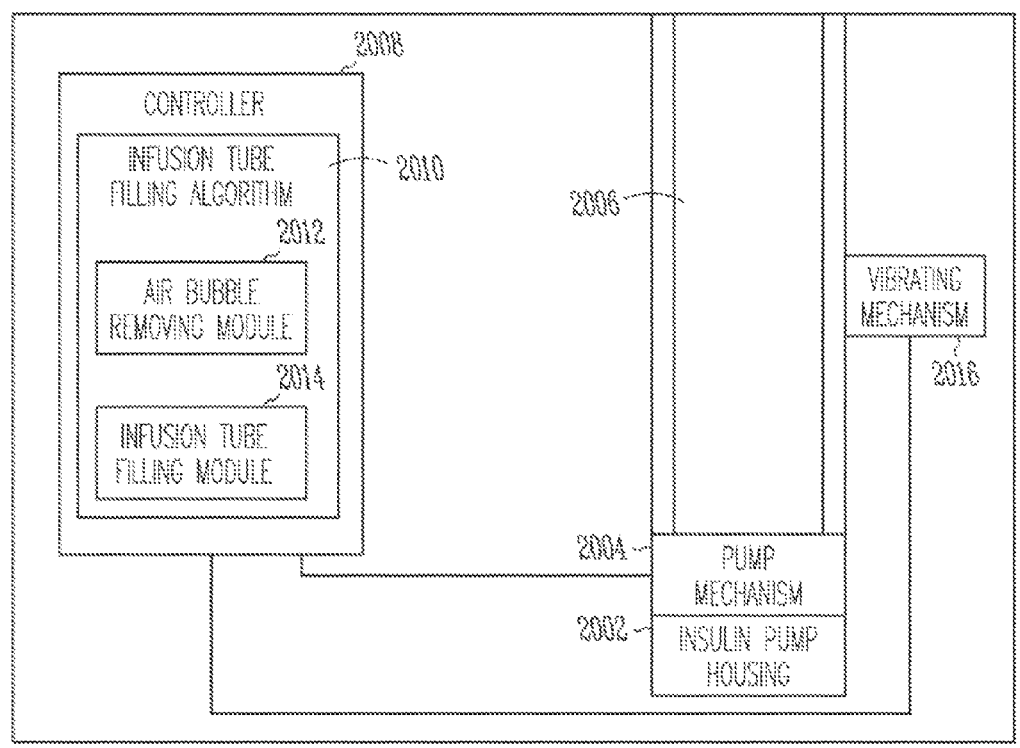
Fig. 20

SYSTEMS AND METHODS TO ADDRESS AIR, LEAKS AND OCCLUSIONS IN AN INSULIN PUMP SYSTEM

RELATED APPLICATION

This application is a continuation of application Ser. No. 12/729,985 filed Mar. 23, 2010, which claims the benefit of U.S. Provisional Application No. 61/165,275, filed Mar. 31, 2009, which is hereby fully incorporated herein by reference.

TECHNICAL FIELD

Insulin pumping systems and detection of air bubbles and occlusions, and remedying of the same.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices.

In some examples, a person using an insulin pump may have an air bubble in the infusion tube extending between the pump and the infusion site on the person. The air bubble has a volume and takes the place of a portion of the basal infusion or bolus designated for the person. The air bubble thereby decreases the accuracy of insulin infusion to the patient and the insulin pump at least fails to properly manage the blood glucose of the person. Alternatively, the person is forced to prime the insulin pump to dispense sufficient insulin through the infusion tube to force out the air bubble. This wastes the insulin between the air bubble and the infusion site.

In still other examples, leaks develop in the insulin pump and the infusion tube set. Leaks make it difficult or impossible to pressurize the insulin and deliver accurate insulin infusions. Similarly, air in the insulin pump, for instance the insulin cartridge, adversely affects pressurization of the insulin and the accuracy of insulin infusions. In yet other examples, the infusion tube set may become clogged with debris such as particulate matter, and prevent or reduce delivery of insulin infusions.

BRIEF DESCRIPTION OF THE DRAWINGS

FIG. 1A is a front view of one example of an insulin pump and infusion tube set.

FIG. 1B is a front view of a user with the insulin pump shown coupled with the body of the user.

FIG. 3A is a side view of one example of an infusion tube set with graduations along the tube to indicate air bubble length and location.

FIG. 3B is a side view of another example of an infusion tube set with graduations along the tube to indicate air bubble length and location, the graduations in units of insulin.

FIG. 6A is a block diagram showing another example of an air bubble compensation method.

FIG. 6B is a block diagram showing one example updating the location and length of an air bubble in an infusion set tube over time.

FIG. 18 is a flowchart further detailing the method for clearing occlusions in the an infusion set tubing including reverse pumping an insulin infusion prior to forward pumping after attempting to clear an occlusion.

FIG. 19 is a flowchart further detailing the method for clearing occlusions in the an infusion set tubing including attempting to deliver an insulin infusion and reversing a pump action a specified amount in the case of an occlusion in the infusion set tube.

FIG. 20 is a schematic diagram of one example of a system for removing air bubbles in an insulin cartridge.

DESCRIPTION OF THE EMBODIMENTS

Figure 2A:
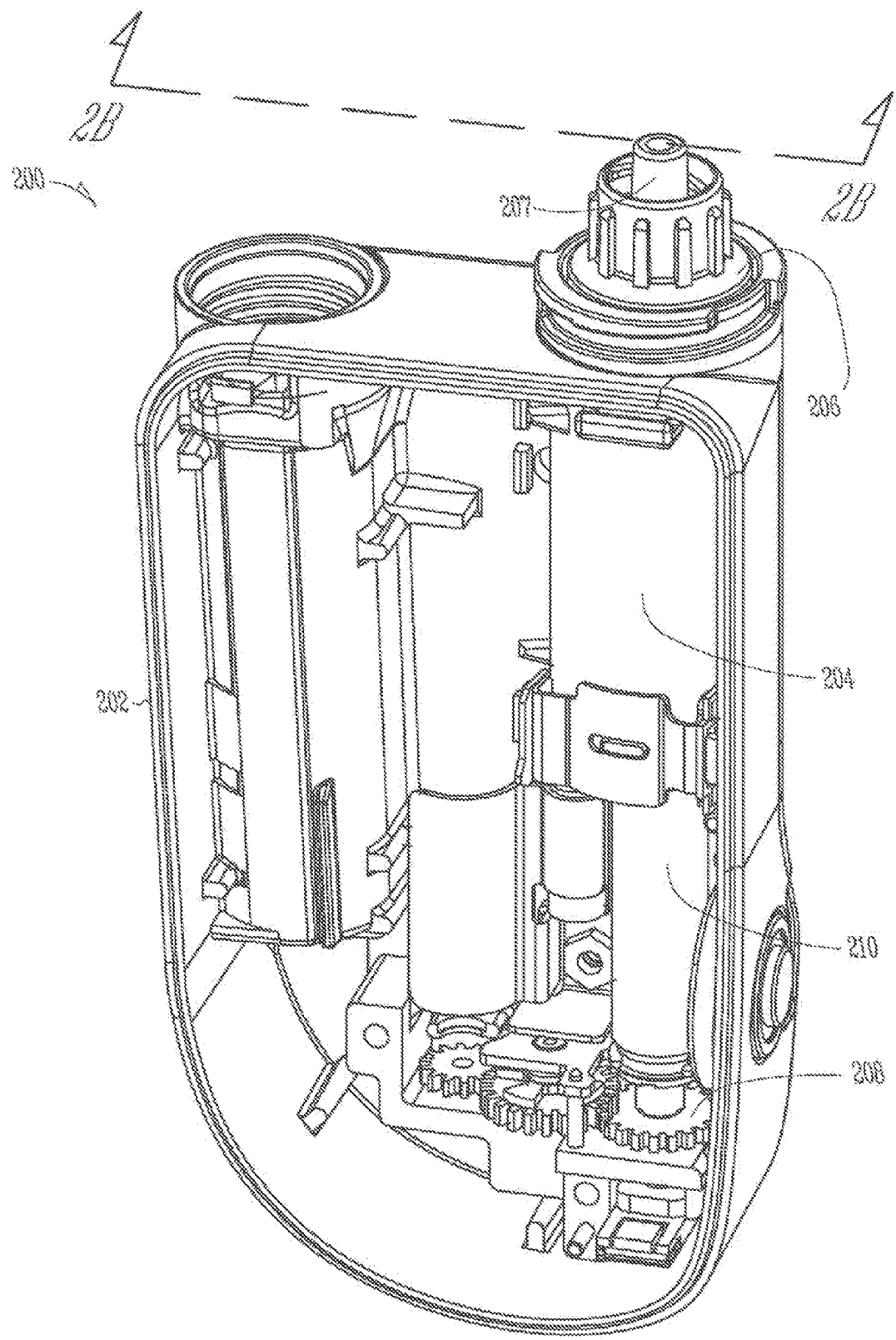
FIG. 2A is a perspective interior view of one example of an insulin pump.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

One example of an insulin pump 100 is shown in FIG. 1A. The insulin pump 100 includes a pump body 106. In one example, the pump body 106 includes a display screen 102 and a data input key pad 104. An infusion tube 140 extends from the insulin pump 100 and is configured for coupling with an infusion site of the user. The infusion tube 140 includes, in one example, a connector 145 sized and shaped for coupling with a fitting implanted on the user.

Referring now to FIG. 1B, the insulin pump 100 is shown positioned on the user 102, for instance positioned on the side of the user 102. The infusion tube 140 extends toward an infusion site 142 where, in one example, the connector 145 is coupled with an implanted fitting coupled with the user 102. In yet another example, the infusion tube 140 includes a needle for injection of insulin from the insulin pump 100 at the infusion site 142.

Figure 2B:
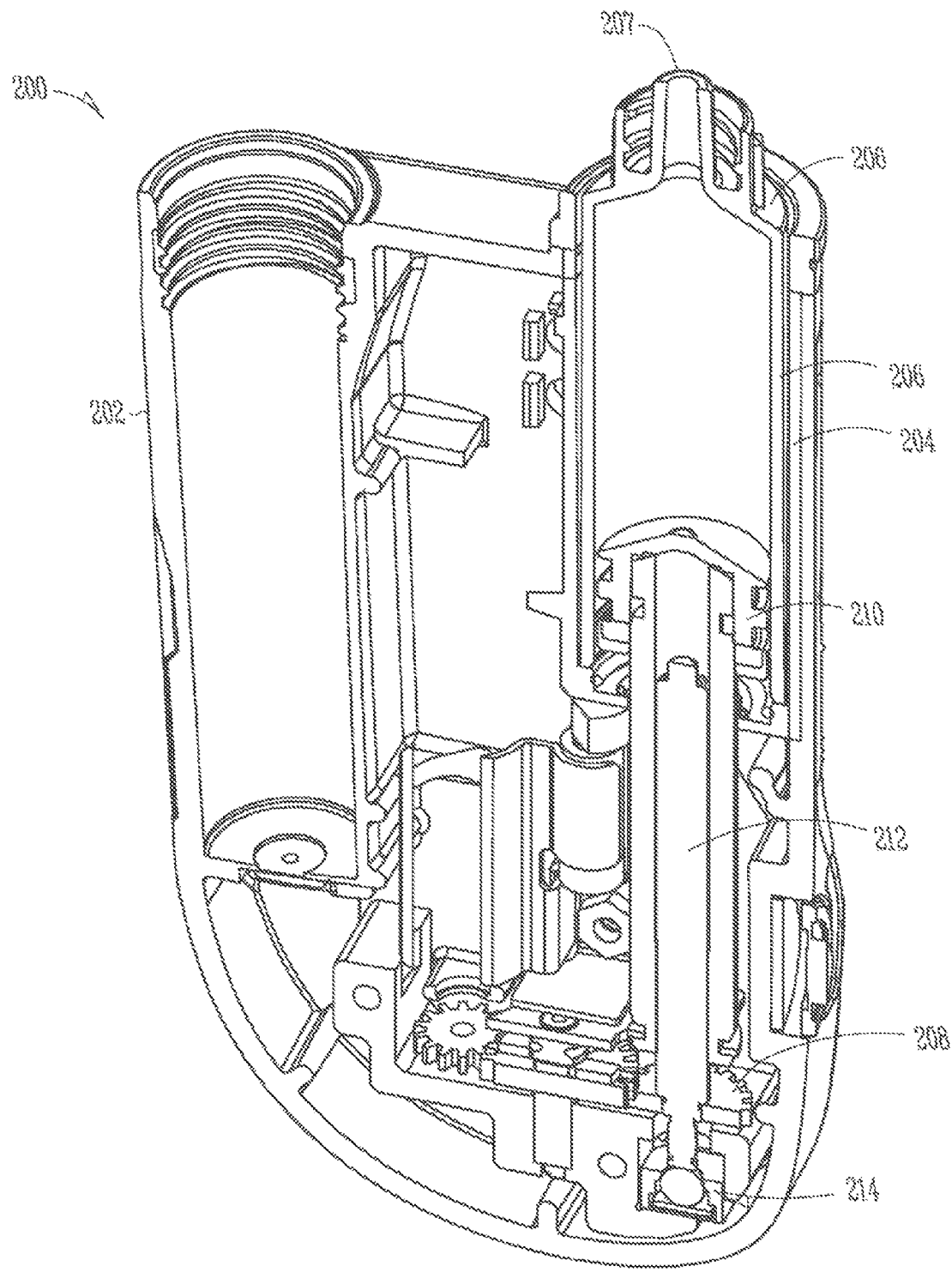
FIG. 2B is a perspective sectional view of the insulin pump taken along line 2B-2B in FIG. 2A.

FIGS. 2A, B show one example of an insulin pump 200. FIG. 2B shows a sectional view of the insulin pump 200 taken along the section line 2B-2B shown in FIG. 2A. Insulin pump 200 includes an insulin pump housing 202 sized and shaped to contain at least an insulin cartridge housing, pump mechanism and controller for operating the pump mechanism to dispense the insulin from the insulin cartridge. An insulin cartridge housing 204 is configured to contain an insulin cartridge 206. As shown in FIGS. 2A, 2B the insulin cartridge 206 includes an infusion tube fitting 207. The infusion tube fitting 207, in one example, is sized and shaped for coupling with infusion sets, such as the infusion tubes 300, 302 shown in FIGS. 3A, B (described below). The insulin cartridge 206 is held within the insulin cartridge housing 204. The insulin cartridge housing 204 holds the insulin cartridge 206 in place while a piston 210 of the pump mechanism 208 is moved into the insulin cartridge forcing the insulin within the insulin cartridge 206 into the infusion tube. Insulin moving through the infusion tube is then infused to the user 102.

Referring now to FIG. 2B, the pump mechanism 208 is shown in sectional detail. As previously described, the piston 210 extends into the insulin cartridge 206. Linear movement of the piston 210 toward the infusion tube fitting 207 forces insulin within the insulin cartridge 206 into the infusion tube and through the infusion tube to an infusion site. In one example, the piston 210 is driven by a rotating pump shaft 212. The pump shaft 212 is rotated by the pump mechanism 208 shown in FIG. 2B. The pump shaft 212 includes threading, and the threading engages the shaft 212 with the piston 210. Rotation of the pump shaft 212 thereby advances the piston 210 linearly through the insulin cartridge 206. Rotation of the pump shaft 212 by the pump mechanism 208 allows for rapid forward and backward movement through rotation of the pump shaft 212. As described below, this rapid movement of the piston 210 allows for removal of occlusions within the infusion tubing and removal of air bubbles within the insulin cartridge 206. Additionally, the rotational interface between the pump shaft 212 and the piston 210 precisely moves the piston 210 within the insulin cartridge 206. The piston 210 is thereby movable in precise increments throughout the cartridge 206. As described below, the piston 210 can be gradually moved both forward into the cartridge and moved backward out of the cartridge 206 to gradually apply pressure to the contents of the insulin cartridge 206. Movement of the piston 210 correspondingly gradually increases (with forward movement) and decreases (with backward movement) the pressure within the environment of at least one of the insulin cartridge 206 and a system of the infusion tube and the insulin cartridge. As described below, the gradual changes in pressure from the movement of the piston 210 are measurable by a pressure sensor within the insulin pump housing 202.

Similarly, the piston 210 can be moved to a specified position within the insulin cartridge 206. Repeatable movement of the piston 210 to the specified position allows for repeated measurements of the pressure within the environment of at least the insulin cartridge 206 and the system of the insulin cartridge 206 and the infusion tube. As described below, pressure measurements taken when the piston 210 is moved to the specified position within the insulin cartridge 206 are used in the detection of leaks within at least one of the insulin cartridge 206 and the system of the insulin cartridge 206 and the infusion tube.

Optionally, the insulin pump 200 uses feedback from the interface between the pump shaft 212 and the piston 210 to measure pressures within the environments of at least one of the insulin cartridge 206 and the system of the infusion tube and the insulin cartridge 206. For instance, as pressure builds within the insulin cartridge 206 because of the piston 210 movement, it is increasingly difficult to rotate the piston shaft 212 relative to the piston 210. The resistance in rotation is measurable by the pressure sensor associated with the pump mechanism 208. Based on the feedback received from the engagement between the piston 210 and pump shaft 212 a pressure measurement is generated by the pressure sensor and communicated to a controller in the insulin pump 200 for use in determining the presence of leaks, air bubbles, occlusions and the like in at least one of the insulin cartridge 206 and the system of the insulin cartridge 206 and the infusion tube. In another example, the pump shaft 212 includes a strain gauge configured to measure deflection of the pump shaft 212 during rotation of the shaft relative to the piston. The measured deflection corresponds to a pressure within the insulin cartridge. Optionally, the strain gauge is positioned adjacent to the pump shaft 212, as shown by the strain gauge 214 shown in FIG. 2B. Engagement of the pump shaft 212 with the strain gauge 214 deflects the strain gauge an amount corresponding to a pressure within the insulin cartridge 206.

Referring now to FIG. 3A one example of an infusion tube 300 is shown having graduations 304 and a connector 145. The graduations 304, in one example, are an accepted format of length measurements including, for instance, the metric or English systems. For instance, the graduation 304 shown in FIG. 3A are in centimeter units allowing measurement of insulin infusion length and corresponding calculation of insulin volumes in the infusion tube 300 (e.g., with the inner diameter for volume calculation and the insulin concentration). In another example, the graduations 304 allow measurement of air bubble location and length in the infusion tube 300 and calculation of air bubble volumes within the infusion tube. As further described below, the location and volume of the air bubbles within the infusion tube 300 are monitored during use of the insulin pump 100.

Referring now to FIG. 3B, another example of an infusion tube 302 is shown having graduations 306. The infusion tube 302 further includes a connector 145. As previously described, the connector 145 is sized and shaped for coupling with an implantable fitting on the user 102. As shown in FIG. 3B, the graduations 306 are measured out along at least a portion of the length of the infusion tube 302 in units of insulin. Graduating the infusion tube 302 in units of insulin allows easy measuring of air bubble length and insulin infusion length because lengths are interchangeable as units of volume. Measurements of the location of the air bubble as well as its length provide corresponding measurements of air bubble volume without the need for additional calculation. The insulin unit graduations 306 thereby provide a quick and easy method for simultaneously assessing the location and length of an air bubble as well as its volume. Additional information including the diameter of the infusion tube 302 and the concentration of the insulin is thereby not needed by the insulin pump controller to determine whether a prescribed bolus will include an air bubble. The controller receives all of the information it needs to make such calculations by inputting the length and location of the air bubble in units of insulin.

Figure 4:
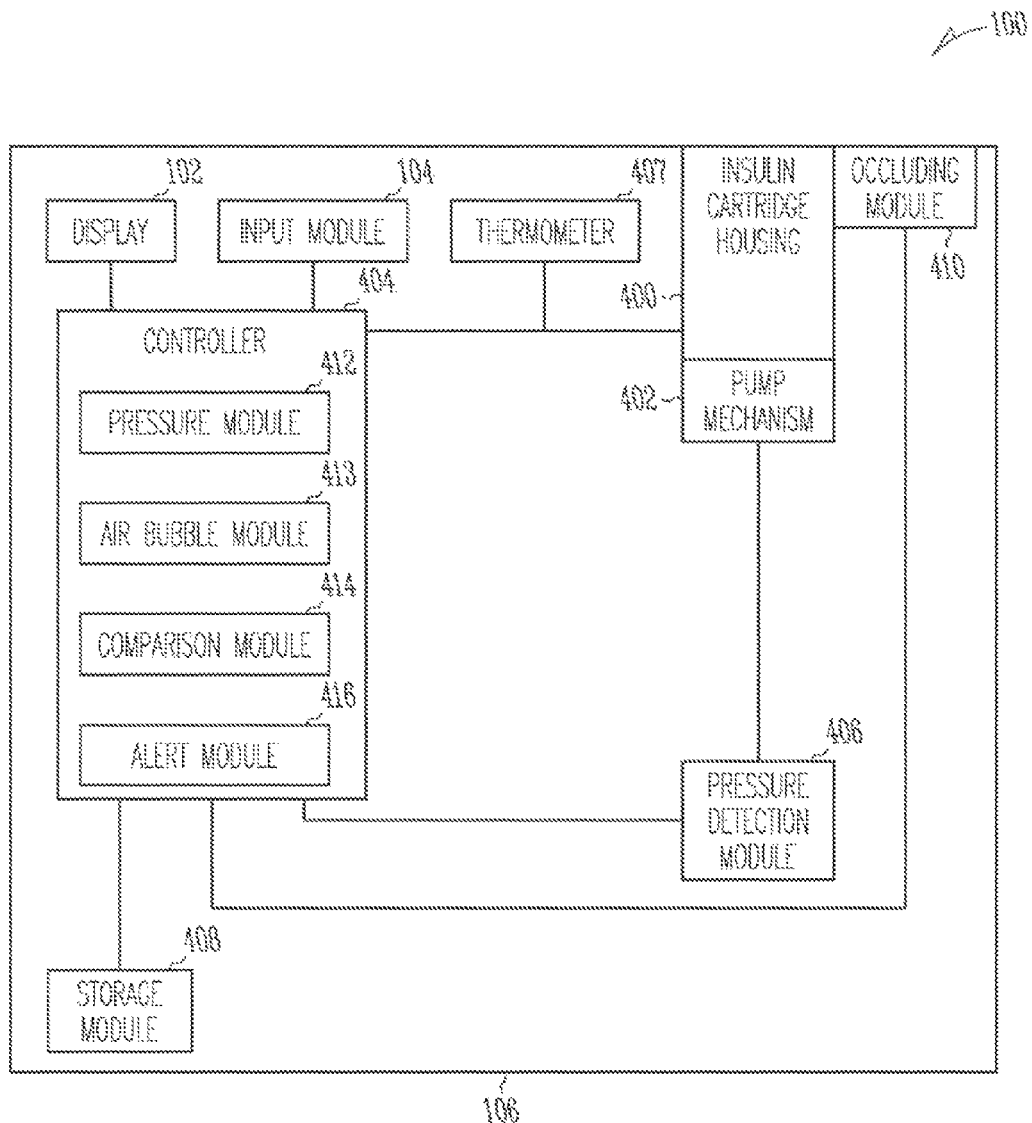
FIG. 4 is a schematic diagram including a series of modules for use with an insulin pump

Referring now to FIG. 4, one example of an insulin pump 100 is shown. The pump 100 includes the insulin pump housing 106 having a variety of components that work to infuse insulin to a user and measure characteristics of the insulin and the system containing the insulin (e.g., the insulin cartridge, infusion tube and the like). An insulin cartridge housing 400 is shown coupled with the pump mechanism 402. In one example, the insulin cartridge housing 400 is a cylindrical orifice within the pump housing 106 sized and shaped to receive an insulin cartridge. The pump mechanism 402, in another example, includes a plunger sized and shaped to move within the insulin cartridge and force insulin out of the insulin cartridge and into the infusion tubing (e.g., the infusion tubing 300, 302 shown in FIGS. 3A, B). A controller 404 is provided to operate the pump mechanism 402 and instructs the pump mechanism to administer basal infusions and insulin bolus infusions as needed according to the controller logic.

In one example, the controller includes a pressure detection module 406 interposed between the controller 404 and the pump mechanism 402. The pressure detection module 406 is configured to detect a pressure within the insulin cartridge during operation of the pump mechanism 402. For instance, the pressure detection module 406 detects pressure within the system of at least one of the insulin cartridge and infusion tube through feedback of the pump mechanism during operation of the insulin pump 100. Optionally, the pressure detection module 406 detects pressure within the system by way of a pressure sensor coupled along the insulin cartridge, such as a piezo-electric element. In another example, the insulin pump 100 includes a thermometer 407 configured to measure the temperature of at least one of the ambient atmosphere around the insulin pump housing 106 and the insulin within the insulin cartridge. The thermometer 407 is coupled with the controller 404, and the controller is configured to adjust thresholds including pressure thresholds, pressure rate of change thresholds and the like according to variations of temperature relative to a base temperature (stored for instance in the storage module 408, described below). As previously described in FIG. 1A, the insulin pump 100 further includes, in another example, a display 102 and an input module 104. The display 102 includes, for instance, a display on the pump 100 as well as a port for connection with a stand-alone monitor or screen system. The input module 104 includes the key pad shown in FIG. 1A as well as an input port for a stand-alone keyboard or other input device.

In yet another example, a storage module 408, for instance, a hard drive, flash memory, and the like is coupled with the controller 404. The storage module 408 is configured to retain and store data generated by the controller 404 (e.g., pressure measurements, insulin usage, temperature measurements), the pressure detection module 406, inputted data from the input module 104 and the like. The storage module stores this information and organizes it for ease of use through the controller and through the display 102. In another example, the pump 100 includes an occluding module 410 sized and shaped to occlude at least one of the insulin cartridge housing 400 or the infusion tube 300, 302. As described further below, the occluding module 410 allows for pressurization of the insulin within the insulin cartridge housing 400. In another example, the occlusion module allows for pressurization of the system of the infusion tube 300, 302 with the insulin cartridge. Occlusion of at least one of the insulin cartridge and the infusion tube allows for pressurization of at least one of the insulin cartridge and infusion tube as a sealed system. As described further below, pressure measurements indicating a variety of conditions, such as air bubbles, leaks and the like are taken from the sealed insulin cartridge and infusion tube.

Modules are retained within the controller 404 including, but not limited to a pressure module 412, an air bubble module 413, a comparison module 414, an alert module 416 and the like. As described below, the pressure module 412 is used to compute pressure rates of change, monitor ambient pressure and the like. The air bubble module 413, in one example, monitors the location of an air bubble within an infusion tube and adds the air bubble volume to an insulin infusion volume as described below. The comparison module 414 is configured to compare measured values (e.g., temperature, pressure, pressure rates of change and the like) with other values including, but not limited to stored threshold values, other measured values and the like. The alert module 416 is configured to provide alerts to the user regarding at least one of a location of an air bubble, the presence of air in the insulin cartridge or infusion tube, the presence of a leak, the presence of blockage in the infusion tube, the status of an insulin infusion and the like. In another example, the controller 404 includes a variety of modules configured to provide control for the operation of the insulin pump 100 used in leak detection, air bubble detection, air bubble monitoring, plug detection, plug and air removal and the like. In yet another example, leak detection information, air bubble location, length and volume, pressure measurement, pressure rates of change, ambient temperature, insulin temperature and the like are stored within the storage module 408 for use by the controller 404. The controller 404 uses this data to operate features of the insulin pump 100 including, but not limited to, the pump mechanism 402, pressure detection module 406, the occluding module 410 and the like. As further described below, the information retained in the storage module 408 is further used in algorithms and methods to measure the location and length of air bubbles, force movement of air bubbles, determine the presence of leaks and flush out plugs within the infusion tube and the insulin cartridge housing.

Figure 5A:
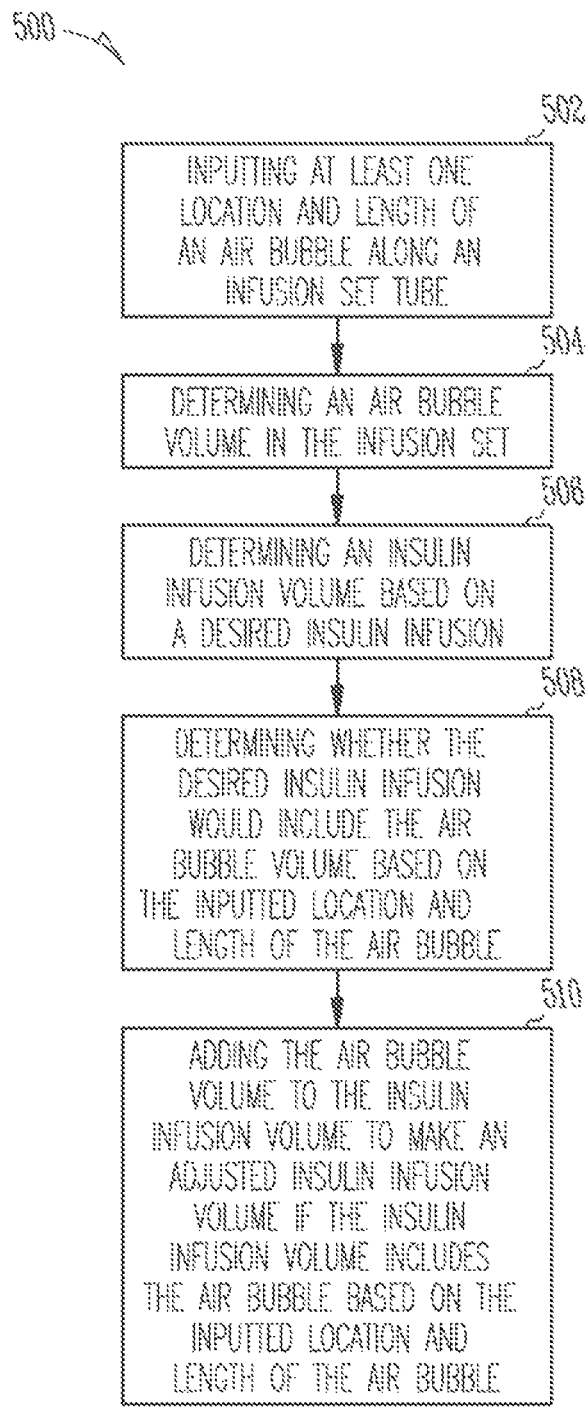
FIG. 5A is a block diagram showing one example of an air bubble compensation method.

FIG. 5A shows one example of a method 500 for compensating insulin infusion volumes that include air bubbles, for instance, within infusion tubes (see the infusion tubes 300, 302 shown in FIGS. 3A, B). At 502, at least one location and length of an air bubble along an infusion tube is input to the insulin pump 100, for instance, through the input module 104. Optionally, the location and lengths of multiple air bubbles within the infusion tube are inputted through the input module 104. At 504, at least one air bubble volume in the infusion tube is determined, for instance by the air bubble module 413. In one example, the air bubble volume is determined by taking the length of the air bubble within the infusion tube, such as the tube 300, and multiplying it by the area generated by computation of the cross-sectional area of the inner diameter of the tube 300. In another example, with the infusion tube 302 having graduations 306 in units of insulin, providing the length of the air bubble correspondingly provides the volume of the air bubble as well. Calculations are thereby avoided because the graduations in units of insulin automatically provide the volume. Where multiple air bubbles are in the infusion tube, multiple air bubble volumes are determined and associated with the respective air bubbles. The controller 404 including the air bubble module 413 performs this association function and stores the air bubble locations, lengths and corresponding volumes within the storage module 408, in still another example.

At 506, an insulin infusion volume is determined based on a desired insulin infusion. In one example, the insulin infusion volume includes a basal insulin infusion. In another example, the insulin infusion volume includes a bolus infusion. In still another example, the insulin infusion volume includes a combination of the basal insulin infusion and bolus insulin infusion.

At 508, the method 500 includes determining whether the desired insulin infusion includes the air bubble volume based on the inputted location and length of the air bubble. In one example, the location and length of the air bubble are compared with a length of the insulin infusion within the infusion tube 300, 302 (see FIGS. 3A, B). For example, the insulin infusion length is measured from a distal end of the infusion tube near the connector 145 shown in FIG. 1A towards the proximal end adjacent to the insulin pump 100. If any portion of the air bubble volume is within this length of the insulin infusion then the air bubble is considered within the insulin infusion. In another example, the air bubble module 413 of FIG. 4 performs the determination.

At 510, if the insulin infusion volume includes the air bubble based on the inputted location and length of the air bubble the air bubble volume is added to the insulin infusion volume to make an adjusted insulin infusion volume (e.g., by the air bubble module 413 within the controller 404). The adjusted insulin infusion volume is thereby a composite volume formed by adding the air bubble volume with the desired insulin infusion volume. The adjusted insulin volume thereby insures that a proper amount of the insulin infusion is actually delivered to the user despite the presence of the air bubble within the infusion tube.

Optionally, if the air bubble is included within the desired insulin infusion an alert may be provided to the user through, for example, the display 102 (e.g., visual display, audible display, vibration, and the like). Once an alert is provided the user is notified of the presence of the air bubble and can monitor the location of the air bubble within the infusion tube as the air bubble moves to near the distal end of the infusion tube (e.g., near the infusion site 140 shown in FIG. 1B). In another example, the controller 404 including the air bubble module 413 monitors the location of the air bubble based on the insulin infusions preceding the air bubble in the infusion tube. An alert is provided when the monitored position of the air bubble is near the infusion site 140. At the connector 145 the user can disconnect the infusion tube and allow the air bubble to cycle out of the tube. The infusion tube is then reconnected to the infusion site to continue the insulin infusion. Disconnecting the infusion tube allows the air bubble to exit the infusion tube while permitting accurate infusion of the desired insulin to the user. Possible complications, including air embolisms and errors in insulin deliver caused by user inaccuracies in estimating bubble sized and location are thereby avoided. The method 500 as described above is retained as at least one of software logic, hardwired circuits and the like within the controller 404.

Several options for the method 500 follow. In one example, determining whether the desired insulin infusion includes the air bubble volume includes determining an insulin infusion length from a distal end of the infusion tube where the infusion tube is graduated in units of volume, for example, from the connector 145 extending proximally toward the insulin pump 100. The insulin infusion volume is used to compute an insulin infusion length by dividing the insulin infusion volume by the cross-sectional area of the infusion tube interior. In another example, determining whether the desired insulin infusion includes the air bubble volume includes comparing the insulin infusion length with the location and length of the air bubble. The desired insulin infusion includes the air bubble volume if any part of the air bubble coincides with any part of the insulin infusion length. Optionally, determining the air bubble insulin infusion volume includes determining the air bubble and insulin infusion volumes in units of insulin. In yet another example, determining the insulin infusion volume includes determining at least one of the basal insulin infusion volume and a bolus infusion volume. In still another example, inputting at least one location and length of an air bubble along the infusion tube includes observing the air bubble relative to the graduations along the infusion tube to determine the location and length of the air bubble. In another option, inputting at least one location and length of the air bubble along the infusion tube includes inputting locations and lengths of a plurality of air bubbles in the infusion tube.

Figure 5B:
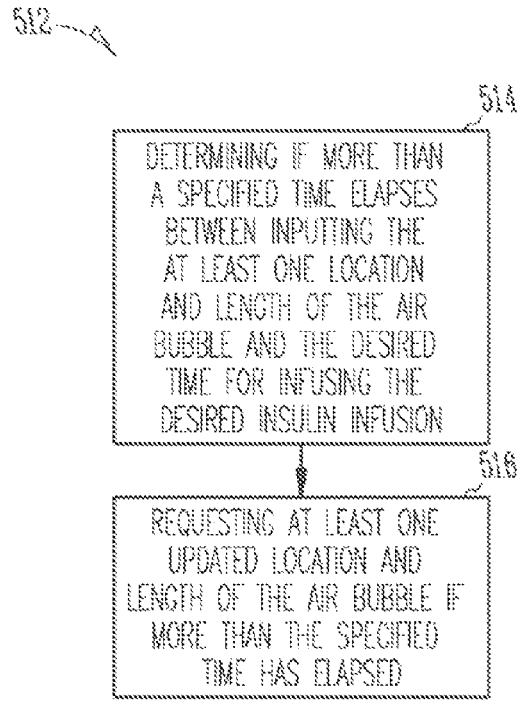
FIG. 5B is a block diagram showing one example of a method for requesting updated air bubble information after a specified time.

FIG. 5B shows one example of a method 512 for updating the location of an air bubble in the infusion tube after a specified amount of time. At 514, the method 512 includes determining if more than a specified amount of time elapses between the inputting of the at least one location and length of the air bubble and the desired time for infusing the desired insulin infusion. (e.g., the specified amount of time includes 15 minutes, 30 minutes, hour and the like). At 516, if more than the specified time has elapsed, the method 512 includes requesting at least one updated location and length of the air bubble due to movement of insulin within the tube or floating of the bubble upstream or downstream. Optionally, the updated location and length are input by at least one of user input or interaction with an automated monitoring module that follows the location of the air bubble in the infusion tube over time.

In one example, the user inputs the updated location and length of the air bubble (e.g., with the input module 104 shown in FIG. 4). In another example, the insulin pump controller 404 shown in FIG. 4 monitors the location of the air bubble, for instance with the air bubble module 413. The air bubble module 413 coordinates with the operation of the pump mechanism 402 to measure the amount of insulin used. As insulin is moved through the infusion tube, the air bubble is correspondingly moved through the infusion tube. The air bubble module 413 thereby is able to monitor the location of the air bubble within the infusion tube based on the amount of insulin dispensed. For example, the air bubble module 413 measures the amount of insulin dispensed in a specified time, computes a corresponding length of that insulin based on the cross-sectional area of the infusion tube, and the monitored location of the air bubble is adjusted an equivalent length according to the computed length of dispensed insulin. In one example, the air bubble module 413 adjusts the location of the air bubble after a specified amount of time has passed (e.g., an interval of at least one of 15 minutes, 30 minutes, an hour and the like). In yet another example, the air bubble module 413 automatically adjusts the location of the air bubble at a set interval including, but not limited to, every minute, every 5 minutes, every half hour, every increment of pump plunger movement for the basal infusion and the like.

Updating the location of air bubbles within the infusion tube after the original inputting of the location and length of the air bubbles ensures accurate location of the air bubbles. Accurate locating of the air bubbles is useful for the purpose of determining whether the air bubble volume should be included with the volume of a pending insulin infusion to ensure the proper amount of insulin is delivered to the user. Additionally, where the controller 404 including the air bubble module 413 monitors the location of the air bubble over time, the user is free to concentrate on other activities without having to observe the air bubble location until immediately before its inclusion in a delivered insulin infusion.

Figure 5C:
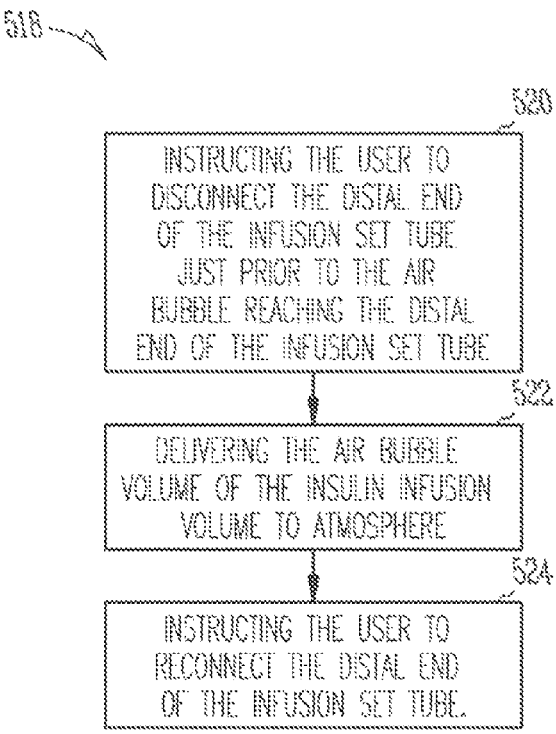
FIG. 5C is a block diagram showing one example of a method for instructing the user to disconnect the infusion set tube when an air bubble is near the distal end of the infusion set tube.

FIG. 5C shows a method 518 of removing an air bubble from an infusion tube without infusing the air bubble to a user. At 520, the user is instructed to disconnect the distal end of the infusion tube just prior to the air bubble reaching the distal end of the infusion tube. In one example, the user disconnects the infusion tube from the infusion site. As previously described, the controller 404 is configured to monitor the location of the air bubble and is thereby aware of the location of the air bubble as it reaches the distal end of the infusion tube, in another example. For instance, as described above in Method 512, the controller 404 including the air bubble module 413 is used to monitor the location and length of the air bubble within the infusion tube as the air bubble moves through the tube. As the air bubble approaches the distal end of the infusion tube near the infusion site 142, the air bubble module 413 cooperates with the alert module 416 and an alert is given to the user providing an option for disconnecting the infusion tube prior to infusion of the air bubble into the user.

At 522, the air bubble is delivered to atmosphere after the infusion tube is removed from the infusion site. After removal of the air bubble, at 524, the user is instructed to reconnect the distal end of the infusion tube to allow continued infusion of insulin including basal insulin infusions and bolus infusions. Optionally, the air bubble module 413 operates the pump mechanism 402 a specified amount to discharge only the air bubble from the infusion tube during the disconnection from the infusion site. As previously described above, because the volume of the air bubble is known (e.g., by way of Method 500), the air bubble module 413 ceases operation of the pump mechanism 402 until the infusion tube is reconnected with the infusion site and an appropriate command is given that normal operation should resume, such as with the input module 104.

The method 518 allows for easy removal of air bubbles within an infusion tube without frequent observation by the user. Because the controller 404 monitors the air bubble location and provides time-specific instructions for disconnecting the infusion tube to allow discharge of the bubble to atmosphere the user is free to concentrate on other activities. Further, removal of the air bubbles from the infusion tube prevents introduction of the air bubbles to the body of the user thereby substantially preventing complications including air embolisms.

Figure 5D:
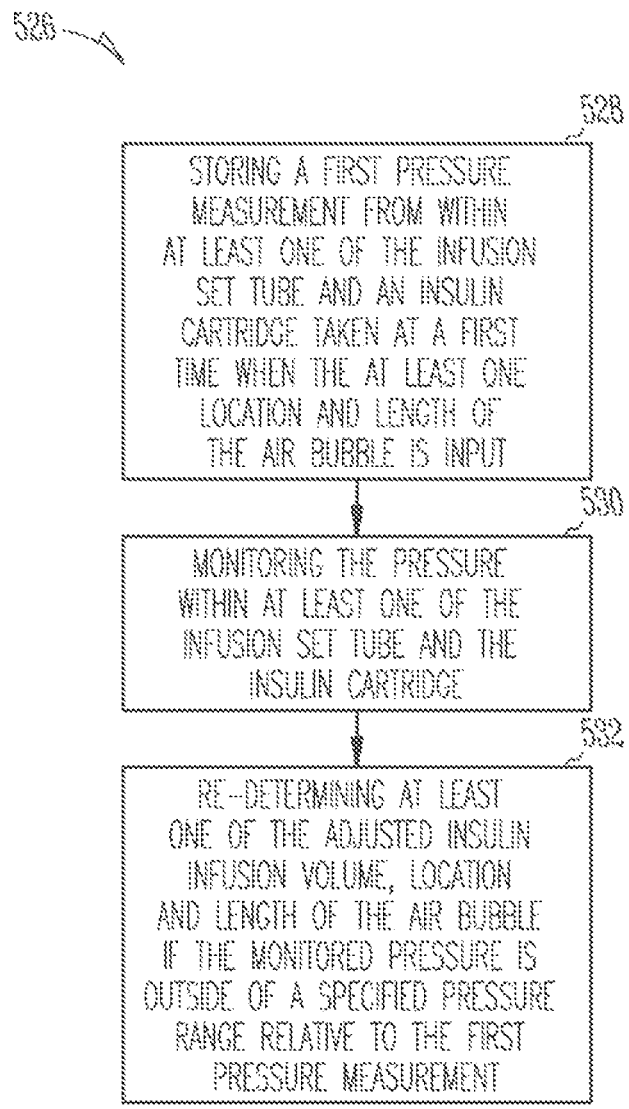
FIG. 5D is a block diagram showing one example of a method for monitoring a pressure in the insulin pump and the infusion set tube and adjusting the location and length of the air bubble if the pressure changes.

Another method 526 for adjusting air bubble location, length and volume based on changes in pressure from a time air bubble characteristics are originally input into the controller 404 is shown in FIG. 5D. At 528, a first pressure measurement from within at least one of the infusion tube and the insulin cartridge is stored after being taken at a first time when the at least one location and length of the air bubble is input, for instance, into the input module 104. In one example, the pressure measurement is associated with the location and length of the air bubble and stored together in the storage module 408. At 530, the pressure within at least one of the infusion tube and the insulin cartridge is monitored. In one example, the pressure within the system of the infusion tube and the insulin cartridge is measured from the time the air bubble location and length are input until dispensing of the insulin infusion containing the air bubble. In another example, the pressure is monitored until the pressure changes outside of a specified pressure range as discussed below. In yet another example, the pressure is monitored for a specified time after entering the location and length of the air bubble. At 532, the method 526 includes redetermining at least one of the adjusted insulin infusion volume, and air bubble location and length (and the corresponding change in air bubble volume based on a change in the bubble length) if the monitored pressure is outside a specified pressure range relative to the first pressure measurement (e.g., a range of plus or minus 0.25 atmospheres relative to the first pressure measurement).

In one example, the controller 404 including the pressure module 412 monitors pressure changes in the insulin cartridge and infusion tube according to changes in atmospheric pressure. In another example, location and length of the air bubble (as well as the volume), and the corresponding adjusted insulin infusion volume would change according to changes in pressure due to occlusions that develop in the infusion tube. Pressure in the system of the insulin cartridge and the infusion tube would increase as the pump mechanism 406 attempts to force insulin around the occlusion. The pressure module 412 can adjust the locations and lengths of the air bubbles based on changes in pressure due to the occlusion to maintain accurate delivery of insulin infusions despite the occlusion. In still another example, the pressure module 412 adjusts the location and length of a plurality of air bubbles previously input to the controller 404. For instance, a length of a first air bubble in the infusion tube closest to the infusion site is redetermined based on the change in pressure. The change in length of the first air bubble correspondingly changes the location of a second air bubble located toward the insulin pump (i.e., the second air bubble is pushed or pulled in the infusion tube by the expanded or shrunk first air bubble). The location of the second air bubble is redetermined based on the change in length of the first air bubble, and the second air bubble length is changed according to the change in pressure.

By recalculating the air bubble length and location (and recalculating the air bubble volume based on the change in length) accurate adjusted insulin infusion volumes are generated for accurate insulin infusions for the user. The user may thereby enter a location and length of an air bubble a single time and rely on the controller 404 and pressure module 412 to adjust the air bubble location and length and the corresponding adjusted insulin infusion volume (see step 510 above in FIG. 5A) to ensure accurate insulin infusions.

Referring now to FIG. 6A, another example of a method 600 for adjusting an insulin infusion volume based on the presence of an air bubble within the insulin infusion is shown. At 602, at least one location and length of an air bubble within an infusion tube is input for, instance, to the input module 104 of the pump 100. At 604, an insulin infusion length is determined from a distal end of an insulin infusion set based on an insulin infusion volume. For example, the desired insulin infusion volume quantity is divided by the cross sectional area of the inner diameter of the insulin infusion tube. This quantity is equivalent to the length of the insulin infusion within the infusion tube used with the insulin pump 100. At 606, the location of the air bubble is then compared with the insulin infusion length. At 608, the air bubble volume is added to the insulin infusion volume to make an adjusted insulin infusion volume if any part of the air bubble coincides with the insulin infusion length previously determined.

FIG. 6B shows one example of a method 610 for updating a location of an air bubble within an infusion tube after a specified amount of time and readjusting the adjusted insulin infusion volume based on the updated location of the air bubble. Method 610 includes at 612 updating a location of the air bubble (or a plurality of air bubbles) if the insulin infusion volume containing the air bubble is not delivered within a specified time after inputting the at least one location length of the air bubble. The instant location of the air bubble is updated based on the previously input air bubble location and length and the insulin delivered in the time between the inputting of the location and length of the air bubble and the scheduled delivery of the insulin infusion volume. In one example, the specified time includes an interval including, but not limited to every set increment of movement of the pump mechanism after inputting of the air bubble location and length, set time intervals independent of the pump mechanism operation and the like.

At 614, the method 610 includes redetermining whether the insulin infusion volume includes the air bubble based on the updated location of the air bubble. In one example, the method 610 is an automatic function of the controller 404 including the air bubble module 413 of the insulin pump 100 shown in FIG. 4. The location of the air bubble is updated over a period of time based on the original inputted location of the air bubble as well as the amount of insulin used over that period of time. That is to say, that as insulin is used the air bubble will necessarily move along the infusion tube toward the distal end where the infusion tube is coupled with the user. The controller 404 redetermines whether an insulin infusion contains the air bubble having the updated bubble location on an on-going basis. For instance, the controller 404 continuously updates the location of the air bubble and correspondingly continuously redetermines whether an insulin infusion, such as at least one of an immediate basal infusion or immediate bolus infusion includes the air bubble. In another example, the controller 404 updates the location of the air bubble and redetermines whether an insulin infusion includes the air bubble on an interval, including, but not limited to, every 30 seconds, every 5 minutes, every half hour, every set increment of movement of the pump mechanism and the like.

In one example, the method 610 is used where the user originally inputs the location of the air bubble at a first time. The air bubble is not within a basal insulin infusion at the time of inputting (e.g., the air bubble is positioned proximally relative to the preceding basal infusion amount) and at a later time the user desires the addition of a bolus infusion. The user enters the amount of the bolus infusion at this later time. The air bubble volume is included in the volume of the bolus infusion because of distal movement of the air bubble toward the infusion site (e.g., from earlier basal and bolus infusions) that now positions the air bubble within the desired bolus infusion. The distal movement of the air bubble occurs between the times of the original inputting of the air bubble location and length and the desired bolus infusion. In yet another example, the air bubble moves along the infusion tube during basal infusion and after some amount of time reaches the distal end of the infusion tube and is included in the basal infusion amount or calculations of the adjusted insulin infusion volume as previously described.

The method 610 allows for early entry of an air bubble location and length such as during insulin cartridge installation and infusion tube priming, and the controller 404 including the air bubble module 413 updates the location of the air bubble and adds the air bubble volume to an insulin infusion at some later time based on the updated location of the air bubble. After entry of the air bubble location and length, the user is free to engage in other activities. Additionally, the user may then later request a bolus infusion from the insulin pump 100 and the controller 404 will add the air bubble location to the bolus infusion as previously described if the updated location of the air bubble is within the infusion. The user does not need to re-input the updated location of the air bubble.

Optionally, the method 610 includes alerting the user to the presence of the air bubble within the insulin infusion volume just prior to the air bubble reaching the distal end of the infusion tube. For instance, the distal end at element 145 (e.g., connector). This provides the user sufficient opportunity to disconnect the distal end of the infusion tube from the infusion site 142 shown in FIG. 1B. The air bubble is then cycled out by pumping of the insulin through the infusion tube allowing the user to then recouple the infusion tube at the infusion site 142 and continue with normal basal and bolus infusion.

Figure 7:
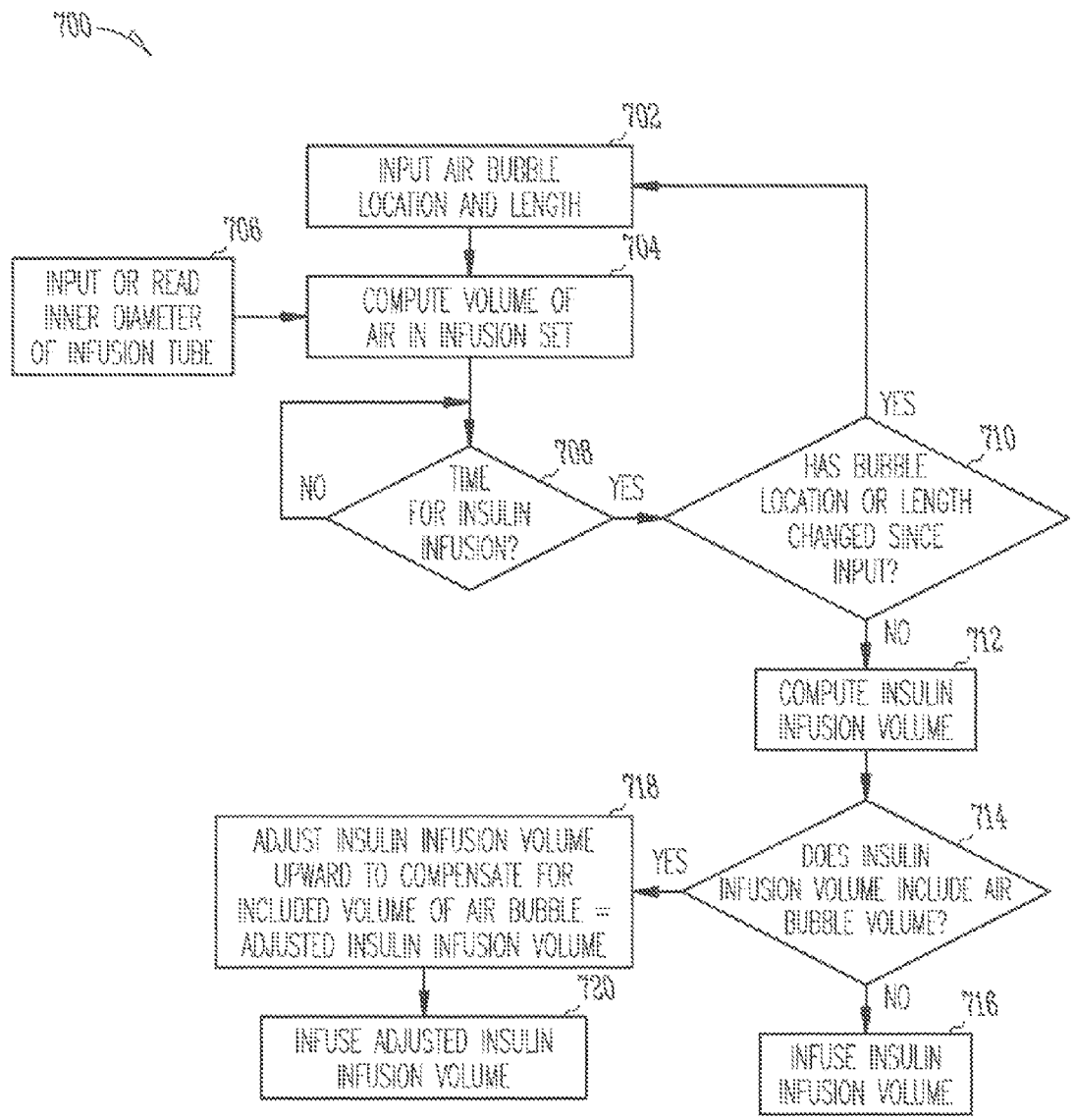
FIG. 7 is a flowchart showing yet another example of an air bubble compensation method.

FIG. 7 shows one example of a method 700 in the form of a flow chart for determining an adjusted insulin infusion volume based on compensation for an air bubble within the infusion tube. At 702, an air bubble location and length are input, for example, into the input module 104 of the insulin pump 100 shown in FIG. 4. At 704, a volume of the air bubble is computed. For example, at 706 the inner diameter of the infusion tube is input or read with a sensor within the insulin pump capable of detecting the inner diameter of the infusion tube. Optionally, the insulin pump 100 includes the storage module 408 having a catalog of infusion tube sizes and corresponding inner diameters for use with the computation of the volume of the air in the infusion tube. As previously described in one example, the volume of the air is computed by multiplying the area of the inner diameter of the infusion tube with the length of the air bubble. In another example, as previously described, the infusion tube, such as infusion tube 302, includes graduations 306 along the length of the tube that measure the air bubble in volumetric units of insulin. When the air bubble location and length are input according to the volumetric graduations 306 the air bubble volume is automatically input. Using the graduations 306 provides a rapid method to locate and determine air bubble volume without needing calculations by the insulin pump. For instance, with the graduations in units of insulin on the infusion tube 302, if a user observes an air bubble that is 2.5 units of insulin proximal to the infusion site, and 0.5 units long the user inserts the corresponding measurements into the insulin pump for determination purposes (see step 708 below). The diameter of the infusion tube is not needed nor are volume computations involving the length of the bubble and the tube diameter.

At 708, a determination is made regarding whether or not it is time for an insulin infusion (e.g., a bolus infusion and the like). If it is not yet time the method 700 continues to cycle over the time determination step 708 until an appropriate amount of time is passed for the infusion to begin. If it is time for the insulin infusion, at 710, a determination is made as to whether or not a location or length of the bubble has changed since the input. If the location or length has changed then the method 700 begins again at 702 allowing re-input of at least one of the air bubble location and length. Optionally, the controller 404 monitors the air bubble location and length and automatically updates the method 700 with regard to the changed air bubble location and length after a set period.

Once the method 700 has cycled through the preceding steps, for instance, 702, 704, 708 and 710, at 712 the insulin infusion volume is computed. As previously described, the insulin infusion volume, in one example, includes the basal infusion, the bolus infusion and the like. At 714, a comparison is made between the locations of the air bubble volume and the insulin infusion volume. This comparison determines whether or not the insulin infusion volume includes any portion of the air bubble volume. If the insulin infusion volume does include a portion of the air bubble volume the insulin infusion volume is adjusted upward to compensate for the included volume of the air bubble creating an adjusted insulin infusion volume at 718. The adjusted insulin infusion volume is then administered to the user at 720. If the air bubble is not included in the insulin infusion volume, at 716, the insulin infusion volume computed in step 712 is then infused to the user.

Figure 8:
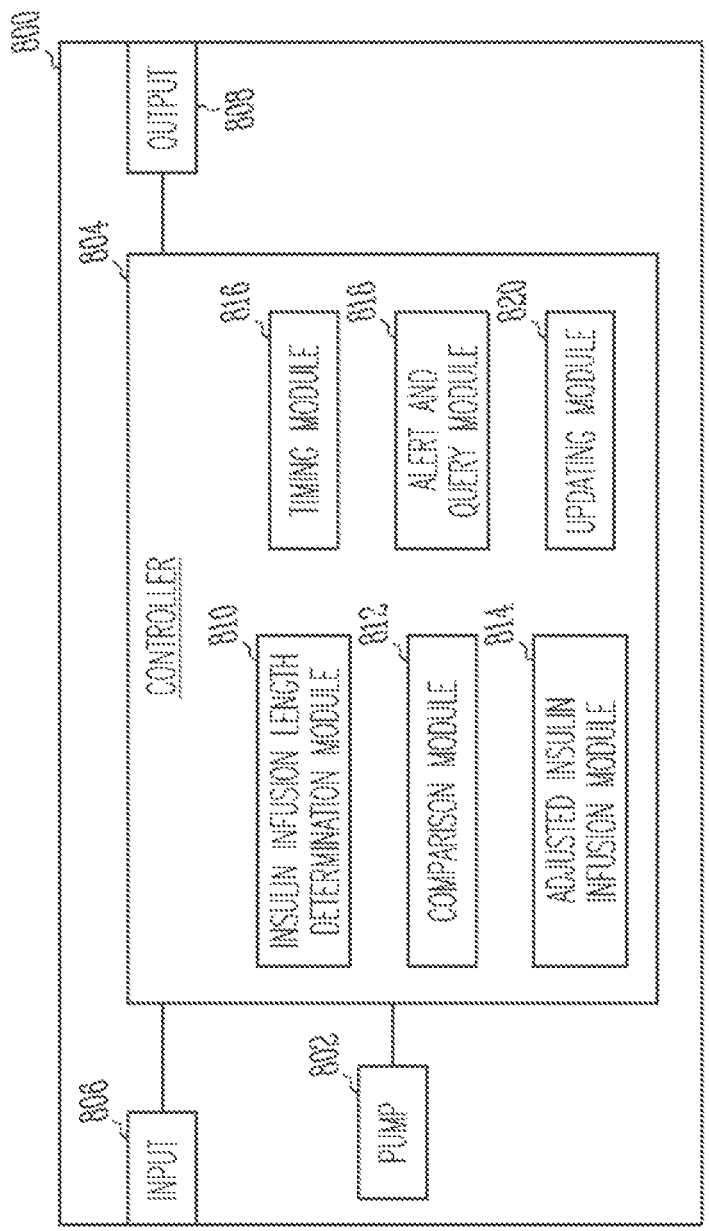
FIG. 8 is a schematic diagram of one example of a system for adjusting insulin infusion amount based on inclusion of air bubbles.

FIG. 8 shows one example of a system 800 for adjusting the insulin infusion amounts based on the inclusion of air bubbles within the insulin infusion. System 800 includes an insulin pump 802, a controller 804 and an input module 806 coupled with the controller. The input module 806, in one example, includes a key pad, input port for receiving input from outside of the system 800, and the like. The system 800 further includes an output module 808 coupled with the controller 804. In one example, the output module includes, but is not limited to, a display screen, a port for coupling with a stand alone display and the like. In another example, the output module 808 includes an audio or vibratory alert module. Controller 804 includes a series of modules (e.g., software modules, hard-wired modules, and the like). The modules within the controller 804 provide the control logic to operate the pump 802 as well as adjust for the presence of an air bubble within a desired insulin infusion amount. An insulin infusion length determination module 810 is shown on controller 804. As previously described, the insulin infusion length determination module 810 takes a specified volume of insulin for infusion to a user and computes a corresponding length within the infusion tube for further comparison with the air bubble location and length. A comparison module 812 takes the location and length of the air bubble and compares it with the insulin infusion length and determines whether or not the insulin infusion will include any portion of the air bubble. The adjusted insulin infusion module 814 adds the volume of the air bubble to the insulin infusion volume to generate an adjusted insulin infusion volume for administration to the user. This adjusted insulin infusion volume is used by the controller to operate the pump 802 and correspondingly deliver a volume of insulin and air through the infusion tube toward the user.

In one example, the controller 804 includes a timing module 816. Timing module 816 is used with the input value for the air bubble length and location to assist in monitoring the air bubble location and length prior to inclusion of the air bubble within the insulin infusion volumes. As previously described in another example, a specified amount of time is passed between the input of the location length of the air bubble and the infusion of the insulin. In one example, the timing module cooperates with the alert and query module 818 to provide an alert to the user requesting additional information on the updated location and length of the air bubble. In yet another example, an updating module 820 is used to update the location of the air bubble as well as its length over a specified amount of time between, for example, the original inputting of the air bubble location and the time of a scheduled delivery of an insulin infusion to the user.

Figure 9:
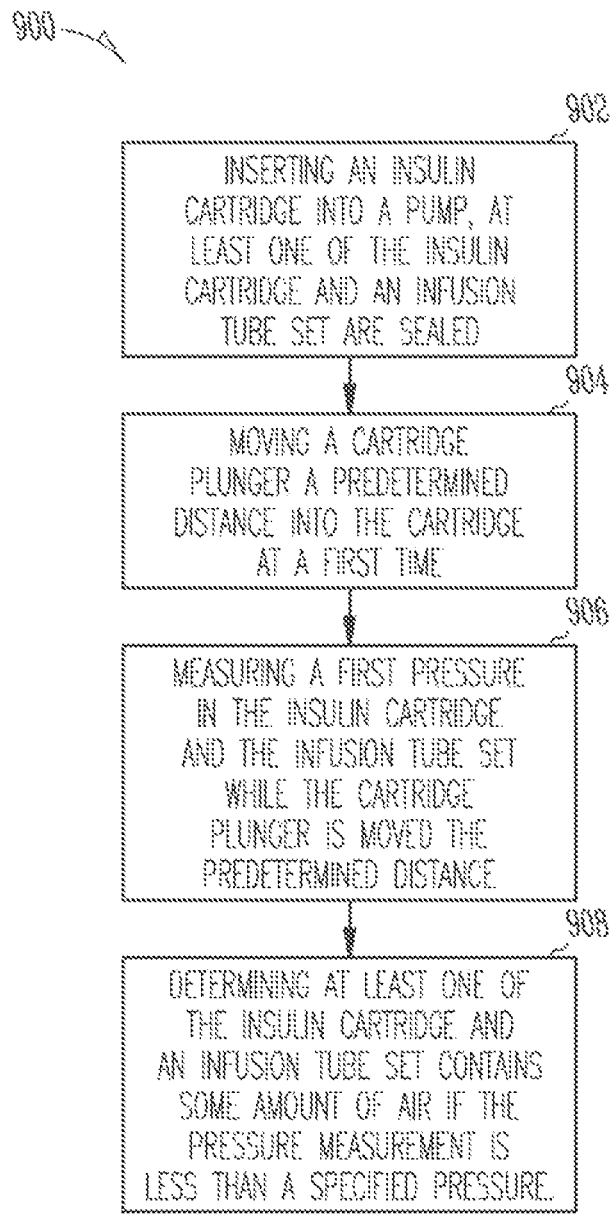
FIG. 9 is a block diagram showing one example of a method for determining the presence of air in an insulin cartridge or infusion tube set.

FIG. 9 shows one example of a method 900 for determining the presence of air in an at least one of an insulin cartridge and infusion tube. At 902, an insulin cartridge is inserted into a pump, such as the insulin pump 100 shown in FIG. 1A. At least the insulin cartridge is sealed at a cartridge discharge opening. Where the presence of air in the insulin cartridge and the infusion tube will be determined, at least the infusion set tube will be coupled with the insulin cartridge and in communication therewith and the system of the infusion tube and the insulin cartridge will be sealed at an infusion tube discharge opening (e.g., at the connector 145 shown in FIG. 1).

At 904, the pump mechanism is operated, for instance, a cartridge plunger is moved a specified distance into the insulin cartridge at a first time. Because at least one of the insulin cartridge and the infusion tube are sealed (at the cartridge discharge or the infusion tube discharge) operation of the pump mechanism generates pressure in at least one of the sealed insulin cartridge and the sealed infusion tube.

At 906, a first pressure generated by the movement of the pump mechanism is measured in at least one of the insulin cartridge and the infusion tube while the cartridge plunger is moved the predetermined distance. In another example, the first pressure is measured in at least one of the insulin cartridge and the infusion tube when the pump mechanism is operated through range of motion. That is to say, pressure is measured and recorded in at least one of the insulin cartridge and the infusion tube throughout the movement of the pump mechanism thereby generating a series of pressure measurement data points.

At 908, the method 900 includes determining that at least one of the insulin cartridge in the infusion tube set contains some amount of air if the pressure measurement is less than a specified pressure, such as a specified pressure stored in the memory module 408 as shown in FIG. 4. In one example, the specified pressure is substantially equivalent to a pressure generated within a sealed insulin cartridge without any air present. In another example, the specified pressure is substantially equivalent to a pressure generated within a system of a sealed insulin cartridge and infusion tube without any air present. Because insulin is relatively incompressible relative to air any difference between the first pressure measurement and the specified pressure, which is based on a system containing only incompressible insulin, is indicative of an air bubble (or air bubbles) within at least one of the insulin cartridge and the infusion tube.

In one example, moving the cartridge plunger includes moving the cartridge plunger a specified distance. This includes gradually moving the plunger over a period of time until the specified distance is reached. Measuring the first pressure in at least one of the insulin cartridge and the infusion tube includes measuring a pressure rate of change in the insulin cartridge in the infusion tube over that period of time. In yet another example, generating the pressure rate of change is performed by performing at least two pressure measurements at two different points within the first period of time. In yet another example, multiple pressure measurements are performed throughout the period of time the cartridge plunger is moved to provide a series of measurements to generate a pressure rate of change having a mathematical function over the period of time. The controller 400 performs comparisons between a specified pressure rate of change and the measured pressure rate of change. Similarly to a single specified pressure modeled on a system without air present in either of the insulin cartridge and the infusion tube, the specified pressure rate of change will have a steep slope (because of the incompressibility of the insulin) relative to a pressure rate of change where air is present in the system.

Several options for the method 900 follow. In one example, inserting the insulin cartridge into the pump and at least one of the insulin cartridge and the infusion tube being sealed includes automatically occluding at least one of the cartridge discharge outlet and the infusion tube discharge outlet. For instance, as shown in FIG. 4, an occluding module 410 is included within the insulin pump 100. The occluding module 410 is sized and shaped to close at least an insulin cartridge discharge opening. In yet another example, the infusion tube such as infusion tubes 300, 302 shown in FIGS. 3A, 3B include occluding mechanisms, for instance, bias clips, slide clamps and the like sized and shaped to engage with the tubes 300, 302 and thereby occlude the tubes so that insulin is unable to flow through the connectors 145. Optionally, the infusion tube occluding mechanisms are selectively positionable along the infusion tubes 300, 302.

In another example, the method 900 includes adjusting the specified pressure based on the elasticity of the infusion tube set. For instance, because of the inherent elasticity of a flexible tube such as the infusion tubes 300, 302 shown in FIGS. 3A, B the specified pressure used to measure against the pressure measurements determined in the method 900 is adjusted according to the rigidity of the material. For instance, where the infusion tube 300, 302 is constructed of a material having less rigidity than, for instance the insulin cartridge, the specified pressure including the specified pressure rate of change is adjusted downward to account for the increased flexibility of the system including the cartridge and the infusion tube (as opposed to solely the insulin cartridge). Measured pressures including measured pressure rates of change taken in a system having increased flexibility (e.g., with the infusion tube) are thereby more accurately compared with a specified pressure calibrated for the increased flexibility.

In yet another example, the specified pressure is based on a benchmark value representative of a system including the infusion tube and the insulin cartridge. When the insulin cartridge is occluded, for instance at the insulin discharge outlet, the infusion tube is separated from the insulin cartridge and is therefore not included in the pressure measurements. The specified pressure (including the specified pressure rate of change) is adjusted upward to account for the increased rigidity of the system of the insulin cartridge by itself. In yet another example, the specified pressure is adjusted upward or downward based on the temperature around the infusion tube and the pump. For instance, the specified pressure (including the specified pressure rate of change) is developed under set conditions such as, room temperature or 70° F./21° C. The system upon which the specified pressure is developed will have increased flexibility in a warm environment and decreased flexibility in a cooler environment relative to the original temperature that the specified pressure or specified pressure rate of change was developed. Adjusting the specified pressure upward or downward thereby allows more accurate comparisons between pressure measurements and pressure rates of change recalibrated for corresponding warmer or cooler climates. For example, in a warmer climate above 70° F. a component of the insulin pump system, such as the infusion tube, may have increased flexibility due to the increased temperature. Pressure measurements taken during a specified pump movement (e.g., movement of an insulin pump plunger) will necessarily be smaller than pressure measurements taken in a more rigid system, for instance, where the infusion tube has more rigid dimensions based on a cooler temperature closer to the benchmark temperature used when originally setting the specified pressure. The lesser pressure measurement in the warmer climate is not necessarily indicative of the presence of air in the system. A comparison of the pressure measurement taken in the warmer temperature with a specified pressure adjusted downward based on the warmer temperature provides a more accurate result thereby avoiding erroneous comparisons between a specified pressure taken at room temperature with pressure measurements or pressure rates of change measured at non-room temperature, for instance, warmer or cooler climates.

In yet another example, the method 900 includes alerting the user to the presence of air in at least one of the insulin cartridge and the infusion tube. Optionally, the user is alerted to the presence of air in the system by vibration, audio alarm, visual alarm and the like. In still another example, the method 900 includes measuring the first pressure in the insulin cartridge with the insulin cartridge sealed relative to the infusion tube. The comparison between the pressure measurement and the specified pressure is performed to determine whether air is present in the insulin cartridge. If the insulin cartridge does not contain air based on the comparison, the insulin cartridge is unsealed allowing communication between the cartridge and the infusion tube. The infusion tube (primed with insulin) is then sealed, for instance at a distal end, and a second pressure measurement is taken and compared with the specified pressure. If the comparison shows the system of the insulin cartridge and the infusion tube contain air, then the previous assessment that air was not present in the insulin cartridge indicates that air is only present in the infusion tube.

Figure 10:
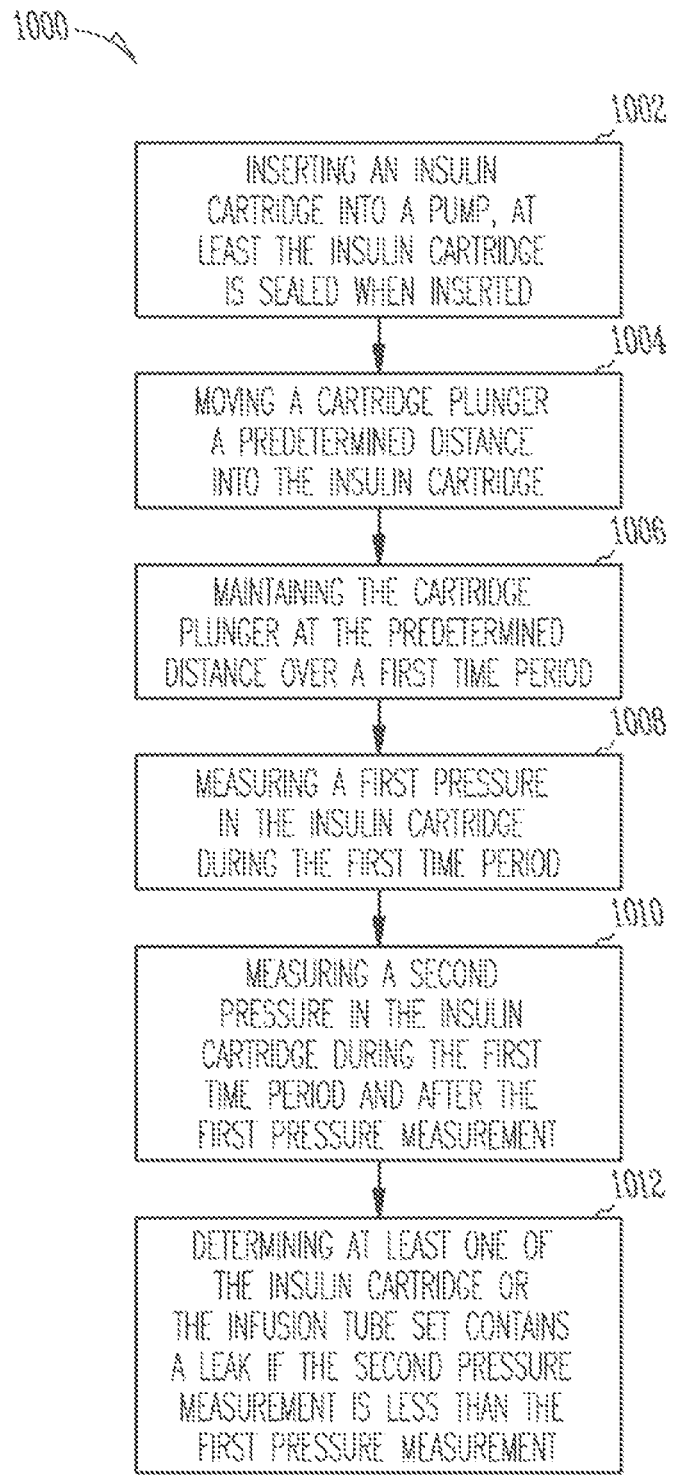
FIG. 10 is a block diagram showing one example of a method for determining the presence of a leak in an insulin cartridge or an infusion tube set.

A method 1000 for determining whether there is a leak in an insulin cartridge or infusion tube is shown in FIG. 10. At 1002, an insulin cartridge is inserted into the pump. When inserted the insulin cartridge is in a sealed state, for example, when the insulin cartridge is inserted into the insulin pump the infusion tube is coupled with the insulin cartridge and at least one end of the infusion tube is occluded thereby sealing the system of the infusion tube and the insulin cartridge. In another example, the insulin cartridge is inserted into the insulin pump and the insulin cartridge is sealed when inserted, for instance, a foil diaphragm is placed over the discharge opening, the discharge opening is closed with a mechanical fitting and the like.

At 1004, a pump mechanism is operated a specified amount, for instance a cartridge plunger is moved a predetermined distance into the insulin cartridge. Movement of the cartridge plunger generates a pressure in the system including at least the insulin cartridge. In another example, cartridge plunger movement generates pressure within the insulin cartridge and the infusion tube where the infusion tube is in communication with the insulin cartridge and otherwise sealed at the infusion tube end (e.g., with bias clip, slide clamp and the like). At 1006, the cartridge plunger is maintained at the predetermined distance over a first time period. The cartridge plunger is maintained at the predetermined distance over the first time period to attempt to maintain a pressure within the insulin cartridge. In another example, the cartridge plunger is maintained at the predetermined distance to maintain a pressure within the system of the insulin cartridge and the infusion tube where the infusion tube is sealed, for instance, with a spring bias clip. In a sealed system without any leaks the maintained position of the cartridge plunger at the predetermined distance should produce a consistent pressure within the system of the insulin cartridge and the infusion tube or the insulin cartridge by itself.

At 1008, a first pressure is measured in the insulin cartridge during the first time period. At 1010, a second pressure is measured in the insulin cartridge during the first time period and after the first pressure measurement. As previously described, the insulin pump 100 is shown in FIG. 4, and in one example includes a pressure detection module 406. The pressure detection module 406 is coupled with the pump mechanism 402 and is able to detect the pressure in the insulin cartridge according to feedback from the pump mechanism 402. In another example, multiple pressure measurements are taken over the first time period and stored in a memory module, such as the memory module 408 shown in FIG. 4. As previously discussed, the system for measuring the pressure includes the insulin cartridge and the infusion tube where the infusion tube is in communication with the insulin cartridge. Measurement of the pressure within the insulin cartridge thereby measures the pressure throughout the system of the insulin cartridge and the infusion tube.

At 1012, a determination is made that at least one of the insulin cartridge or the infusion tube contains a leak if the second pressure measurement is less than the first pressure measurement. That is to say, the second pressure measurement (taken after the first pressure measurement) is less than the first pressure measurement where the cartridge plunger is maintained at the predetermined distance over the first period. When the second pressure measurement is substantially similar to the first pressure measurement an indication is made that at least one of the insulin cartridge and the sealed system of the insulin cartridge and infusion tube are relatively air tight and therefore should not leak insulin during use of the insulin pump. As described above with method 900, adjustments are made to the comparison to account for the elasticity of the plastic components of the tube and the insulin cartridge. For instance, in an elastic system where there is no leak the second pressure measurement may be less than the first pressure measurement due to the expansion of the system over the time period between the two measurements. In one option, the comparison is recalibrated based on the elasticity of the system. In another option, a thermometer (e.g., thermometer 407 shown in FIG. 4) associated with the system further recalibrates the comparison according to relatively higher ambient temperatures with corresponding increased system elasticity and lower ambient temperatures with decreased system elasticity.

As discussed above, a change in pressure (e.g., between the first and second pressure measurements) where the plunger is maintained at a predetermined distance over the first time period indicates that there may be a leak within at least one of the insulin cartridge and the system of the insulin cartridge and the infusion tube where the infusion tube is in communication with the insulin cartridge. Optionally, the user is alerted and instructed to change out the infusion tube and attach the tube with the insulin cartridge and the method 1000 is repeated. If the first and second pressure measurements are consistent over the first time period the user has confidence that the leak was in the infusion tube and may proceed with normal use of the pump. Where the second pressure measurement continues to be less than the first pressure measurement the user has an indication that the leak is in the insulin cartridge and is instructed to exchange the leaking insulin cartridge with a fresh insulin cartridge.

Optionally, the method 1000 is performed as a start up procedure when any insulin cartridge is coupled with the insulin pump 100. The controller 404 of the insulin pump 100 automatically performs a leak detection diagnostic on the insulin cartridge after installation within the insulin pump 100. In another example, the controller 404 automatically performs a leak detection diagnostic on the system of the insulin cartridge and infusion tube once the controller receives confirmation that the infusion tube is occluded (e.g., through an input confirmation entered in the input module 104).

Several options for the method 1000 follow. In one example, inserting the insulin cartridge into the pump includes automatically occluding at least one of the insulin cartridge outlet and an infusion tube. As previously discussed, an occluding module 410 is shown in FIG. 4. The occluding module 410 is sized and shaped to occlude at least the insulin cartridge. In another example, the infusion tube, such as infusion tubes 300, 302 shown in FIGS. 3A, B, includes an occluding element such as a spring bias clip, slide clamp, a kinking feature and the like sized and shaped to occlude the infusion tube when pressure measurements are taken across the system including the infusion tube and the insulin cartridge.

In another example, moving the cartridge plunger the predetermined distance into the insulin cartridge includes moving the cartridge plunger until a goal pressure is reached. In one example, the goal pressure includes the first pressure measurement described in step 1008 above. In yet another example, moving the cartridge plunger the predetermined distance into the insulin cartridge includes moving the cartridge plunger a specified plunger distance. The first pressure measurement taken in step 1008 is thereafter taken once the cartridge plunger has moved the specified plunger distance. The first pressure measurement thereafter acts as the baseline pressure for comparison with the second pressure measurement taken thereafter.

In still another example, the method 1000 further includes unsealing the insulin cartridge after insertion and occluding the infusion tube at a location near the infusion tube distal end, for instance, near the connector 145 shown in FIGS. 3A, B. Optionally, the method 1000 further includes measuring the second pressure in at least one of the insulin cartridge and the system of the cartridge and the infusion tube after a specified interval including, but not limited to, 5 seconds, 30 seconds, one minute and the like.

Figure 11:
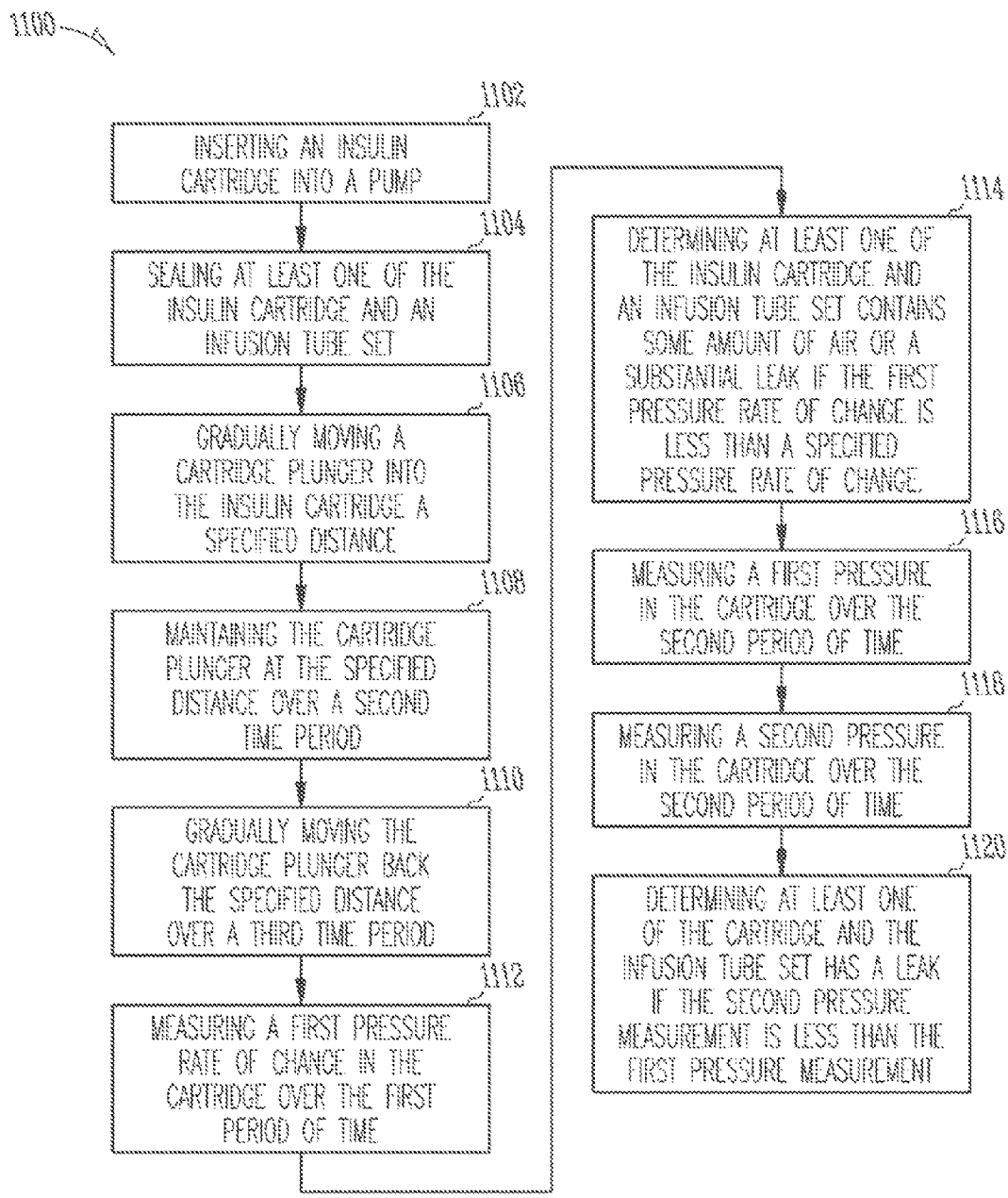
FIG. 11 is a block diagram showing one example of a method for determining the presence of air and leaks in an insulin cartridge or an infusion tube set.

Method 1100 for determining the presence of air and leaks within an insulin cartridge and infusion tube is shown in FIG. 11. At 1102 an insulin cartridge is inserted into an insulin pump such as the insulin pump 100 shown in FIG. 1A. At 1104, at least one of the insulin cartridge and an infusion tube are sealed. In one example, where pressure measurements are to be taken only in the insulin cartridge, the insulin cartridge is sealed (e.g., is inserted within the pump sealed, closed by coupling with the pump when inserted and the like). In another example, where pressure measurements of the insulin cartridge and the infusion tube are to be taken the infusion tube is coupled with the insulin cartridge and in communication with the contents of the insulin cartridge. The infusion tube is thereafter sealed, for instance, at a distal end near the connector 145 shown in the infusion tubes 300, 302 in FIGS. 3A, B. The infusion tube as previously described may be occluded with a spring bias clip, a kinking device and the like. Sealing at least one of the cartridge and the infusion tube provides a sealed system. Variations of pressure within the sealed system should thereby be caused by air or leaks within the system given the occlusion of any discharge points in the infusion tube and insulin cartridge.

At 1106, a cartridge plunger is gradually moved into the insulin cartridge a specified distance. The cartridge plunger is gradually moved into the insulin cartridge over a first time period. In another example, a pump mechanism is operated to operate the pump a specified amount. Operation of the pump mechanism including movement of the cartridge plunger generates a pressure within the sealed system of the insulin cartridge and the infusion tube where the infusion tube is in communication with the insulin cartridge, as described above and herein below. Pressure measurements are taken from the sealed system to assess the presence of air bubbles and leaks within the sealed system within the insulin cartridge and infusion tube. At 1108, the cartridge plunger is maintained at the specified distance over a second time period. At 1110, the cartridge plunger is gradually moved back the specified distance over a third time period. In one example, moving the cartridge plunger back the specified distance moves the cartridge plunger into a neutral position where the insulin cartridge is under the original pressure within the insulin cartridge when installed in the insulin pump. Gradually moving the cartridge plunger the specified distance over the first time period and the second time period allows evaluation of pressures within the sealed system of at least the insulin cartridge, and in another example, the insulin cartridge and the infusion tube over those specified periods. As described below, pressure measurements taken over the first time period indicate whether or not air is present in the sealed system of the insulin cartridge of at least one of the insulin cartridge in the infusion tube. Additionally, pressure measurements taken over the first time period indicate whether a significant leak is present in the system (e.g., pressure fails to rise during operation of the pump or rises a negligible amount). Maintaining the cartridge plunger at the specified distance over the second time period allows for detection of leaks within the sealed system of at least one of the insulin cartridge and the infusion tube. For instance, smaller leaks are detectable that do not immediately preclude development of pressure in the system during the first time period.

At 1112, a first pressure rate of change in the cartridge is measured over the first time period. At 1114, a determination is made that at least one of the insulin cartridge and the infusion tube (where the infusion tube is in communication with the insulin cartridge) contains some amount of air or a substantial leak if at least one of the first or second pressure rates of change is less than a specified pressure rate of change. Where air is in the sealed system of at least one of the insulin cartridge and the infusion tube at least one of the first or second pressure rates of change will be less than the specified pressure rate of change because of the compressibility of air. In the case of a substantial leak, the first pressure rate of change will approach zero and indicate that the system (at least one of the infusion tube set or the insulin cartridge) has a leak large enough to prevent pressurizing of the system (beyond negligible pressurizing). The near zero pressure rate of change is used in one example to differentiate between a substantial leak and air in the system as the system with air will have a greater pressure rate of change than the near zero rate of change indicative of a substantial leak. Where air or substantial leaks are not present in the system of at least one of the insulin cartridge in the infusion tube the system should only include insulin, a relatively incompressible substance. Therefore, the first and second pressure rates of change should be substantially similar to the specified pressure rate of change.

At 1116, a first pressure in at least one of the insulin cartridge and the infusion tube is taken over the second period of time. At 1118, a second pressure in the cartridge is measured over the second period of time. At 1120, a determination is then made that at least one of the cartridge and the infusion tube (where the infusion tube is in communication with the cartridge) has a leak if the second pressure measurement is less than the first pressure measurement. That is to say, in a sealed system where at least one of the insulin cartridge and the infusion tube are without leaks pressure maintained over a period of time should remain substantially the same. Where a leak is present, insulin is able to escape the system through the leak and the pressure in the system over the second period of time should thereby decrease with discharge of the insulin through the leak. A leak detect over the second time period and not in the first time period is smaller leak relative to the large leaks detected in the first time period. The smaller leak is detected by the gradual decrease in pressure measurements over the second time period in contrast to the near zero pressure rate of change indicative of a large leak detected in the first time period.

In one example, the method 1100 includes occluding at least one of the insulin cartridge outlet and an infusion tube prior to gradually moving the cartridge plunger into the insulin cartridge. For instance, the insulin pump 100 includes an occluding module 410 configure to automatically occlude the insulin cartridge upon installation within the insulin pump 100. In another example, the infusion tube includes a feature such as, but no limited to, a spring bias clip, a kinking mechanism, and the like sized and shaped to kink the infusion tube, for instance, near the distal end (e.g., connector 145 shown in FIGS. 3A, B). Optionally, the infusion tube is automatically occluded until connected to the infusion site, for instance with at least one of a pierceable septum, valve and the like.

In still another example, gradually moving the cartridge plunger into the insulin cartridge includes moving the cartridge plunger into the cartridge until a goal pressure is reached. As previously described, in one example, the goal pressure serves as the first pressure measurement used over the second period of time. The first pressure measurement thereby serves as the benchmark against which the second pressure measurement is compared to detect leaks. Where the goal pressure is not reached, for instance where a large leak is present in the system, the cartridge plunger is moved a specified distance. In combination, the cartridge plunger would move advance until the goal pressure is reached or the plunger has moved a specified distance, whichever comes first.

The method 1100 thereby provides a system of steps configured for use with the operation of the pump mechanism, such as the pump mechanism 402 shown in FIG. 4. The pump mechanism generates a pressure within the sealed system of the insulin cartridge and the infusion tube to determine whether or not air or leaks are present within the system. By combining the gradual movement of the cartridge plunger in a first time period with a maintenance period over a second time period both functions of detecting the presence of air and the presence of leaks are performed in a single operation cycle of the insulin pump 100.

Figure 12:
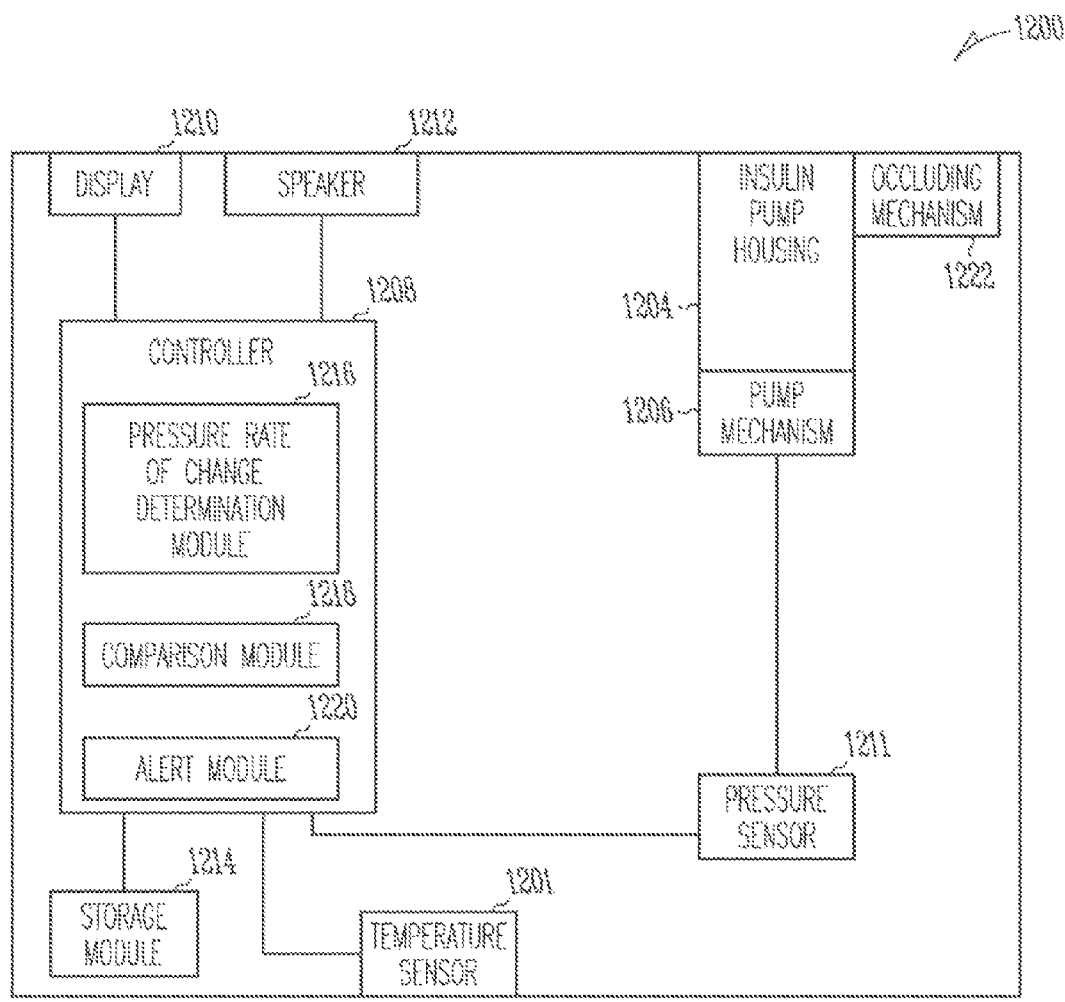
FIG. 12 is a schematic diagram of one example of a system for determining the presence of air in an insulin cartridge or an infusion tube set.

One example of an insulin pump 1200 is shown in FIG. 12. Insulin pump 1200 includes a pump housing 1202 having an insulin cartridge housing 1204 coupled with a pump mechanism 1206. In one example, the pump mechanism 1206 includes a pump having a plunger, the plunger is sized and shaped to move within the insulin cartridge when the insulin cartridge is disposed within the insulin cartridge housing 1204. The plunger of the pump mechanism 1206 forces the insulin within the insulin cartridge out of a discharge within the insulin cartridge and through an infusion tube such as the infusion tubes 300, 302 shown in FIGS. 3A, B.

A controller 1208 is coupled with the pump mechanism 1206. Controller 1208 is configured to operate the pump mechanism 1206 and move insulin out of the insulin cartridge and through the infusion tubing to an infusion site on the user. In one example, a display 1210 is coupled with a controller 1208. Optionally, the display 1210 includes a port on the insulin pump housing 1202, the port is sized and shaped to couple with a free standing display or other output device capable of presenting data on the insulin pump 1200 to a user. A speaker 1212 is coupled with the controller 1208 in another option. The speaker 1212 provides audio alerts and information to the user regarding the functionality of the pump mechanism and operation of the controller 1208. In yet another example, an occluding mechanism 1222 is coupled adjacent to the insulin cartridge housing 1204. As previously described, the occluding mechanism 1222 occludes at least a discharge opening of the insulin cartridge when the insulin cartridge is disposed within the insulin cartridge housing 1204.

In still another example, the occluding mechanism 1222 is operable to engage with a portion of the infusion tubing such as the infusion tubes 300, 302 shown in FIGS. 3A, B. The occluding mechanism 1222 is sized and shaped to couple around at least a portion of the infusion tube and occlude the infusion tube. As previously described, occlusion of the infusion tube when in communication with the insulin cartridge allows pressure measurements including measurements of pressure rates of change within the insulin cartridge and the infusion tube.

The controller 1208 includes modules for assessing data such as pressure sensor data in order to determine the presence of air within the insulin cartridge and infusion tube. In another example, the modules of the controller 1208 are configured to determine the presence of air within the insulin cartridge where the insulin cartridge is sealed by the occluding mechanism 1222 or installed in a sealed manner.

As shown in FIG. 12, a pressure sensor 1211, in one example, is coupled between the pump mechanism 1206 and the controller 1208. The pressure sensor 1211 is configured to measure pressures in the insulin cartridge. In another example, the pressure sensor 1211 is configured to measure pressures within the insulin cartridge and the infusion tube where the infusion tube and insulin cartridge are in communication, for instance, where a seal between the two has been removed. In one example, the pressure sensor 1211 is able to detect pressures by feedback from the pump mechanism 1206. In another example, the pressure sensor 1211 is configured to directly measure a pressure from the insulin cartridge, for instance, with a piezo-electric element coupled along the insulin cartridge housing or in engagement with the insulin cartridge when the insulin cartridge is positioned within the insulin cartridge housing 1204. The data from the pressure sensor 1211 is communicated with the controller 1208. The data from the pressure sensor 1211 includes, in one example, pressure measurements, and pressure measurements used in developing pressure rates of change and the like.

As shown in FIG. 12, the controller 1208 includes a pressure rate of change determination module 1216. The pressure measurements taken by the pressure sensor 1211 are collected by the pressure rate of change determination module 1216 and the controller 1208. The pressure rate of change determination module 1216 uses the pressure measurements to construct a pressure rate of change over a specified period of time. A comparison module 1218 takes the pressure rate of change and compares it against a specified pressure rate of change. As previously described, if the measured pressure rate of change is less than a specified pressure rate of change an indication is given through an alert module 1220 that air is present in at least one of the system of the insulin cartridge and the infusion tube. In one example, the alert module 1220 provides alerts to the user through at least one of the display 1210 and speaker 1212. In still another example, the insulin pump 1200 includes a temperature sensor 1202 (e.g., thermometer, thermocouple and the like) in communication with the controller 1208. The controller 1208 uses temperature measurements from the temperature sensor 1201 to recalibrate the specified pressure rate of change to account for the increasing and decreasing elasticity of the system of at least one of the insulin cartridge and infusion tube due to corresponding rising and falling temperatures.

Optionally, the pressure measurements and pressure rates of change generated by the pressure sensor 1211 and pressure rate of change determination module 1216 are stored in a storage module 1214. For instance, the pressure measurements taken by the pressure sensor 1211 over time are stored in the storage module 1214 as the pressure rate of change is generated on a rolling basis. The pressure rate of change determination module 1216 is thereby able to access the most recent pressure measurements in the storage module 1214 for use in determining a current pressure rate of change.

In operation, a user inserts an insulin cartridge within the insulin cartridge housing 1204. In one example, the insulin cartridge is in a sealed condition. In another example, the insulin cartridge is open and an occluding mechanism, such as occluding mechanism 1222, is operated to occlude the insulin cartridge. In yet another example, the occluding mechanism 1222 occludes a portion of the infusion tubing, such as infusion tubes 300, 302 previously shown in FIG. 3A, B. Occlusion of the infusion tube where the infusion tube is in communication with the insulin cartridge allows the insulin cartridge and the infusion tube to form a sealed environment for pressure measurements, as discussed above.

The pump mechanism 1206, in one example, moves a plunger into the insulin cartridge to push insulin through the infusion tube to an infusion site. Movement of the pump plunger into the insulin cartridge generates a pressure within a sealed system, including but not limited to the insulin cartridge or the insulin cartridge in combination with the infusion tube. The pressure sensor 1211 measures the pressure and communicates the pressure measurement to the controller 1208. As previously described in other examples, multiple pressure measurements are taken by the pressure sensor 1211 over time and are stored in the storage module 1214. The pressure rate of change determination module 1216 within the controller 1208 takes the measurements stored in the storage module 1214 and generates a pressure rate of change. The pressure rate of change is then compared against a specified pressure rate of change in the comparison module 1218. The specified pressure rate of change, in one example, is stored in the storage module 1214. In yet another example, multiple specified pressure rates of change are stored in the storage module 1214. The storage module 1214 stores a catalog of specified pressure rates of change (e.g., for various altitudes, various temperatures, various combinations of pressures and temperatures and the like) and depending on the environmental conditions an appropriate specified pressure rate of change is chosen by at least one of the controller 1208 or a user.

Where the measured pressure rate of change is compared against the specified pressure rate of change and the measured rate is less than the specified rate air may be present in the system of at least one of the insulin cartridge or the insulin cartridge the and infusion tube. An alert is sent by the alert module 1220 to at least one of the display 1210 and the speaker 1212 alerting the user that there may be air present in the system. Optionally, the alert module 1220 communicates a message by at least one of the display 1210 and speaker 1212 instructing the user to find (visually) the air in the system and remove the air from the system by using the priming feature of the pump. In another option, the alert module 1220 requests that the user change out the infusion tube. In yet another option, the alert module 1220 requests that the user change out the insulin cartridge.

In one example, the evaluation of air in at least one of the insulin cartridge or the system of the insulin cartridge and infusion tube is performed automatically upon the insertion of a new insulin cartridge within the insulin pump housing 1202. Where the insulin pump 1200 indicates that there is air present in the insulin cartridge after its installation within the insulin pump housing 1202 the user removes the insulin cartridge and replaces that cartridge with a new insulin cartridge, and the insulin pump 1200 performs the same assessment on the new insulin cartridge. The user is thereby able to have a measure of confidence that air is not present in the system of at least the insulin cartridge. In another example, where the system includes the insulin cartridge in communication with the infusion tube, the automatic detection of air within the system similarly provides confidence that the system is free of air.

Figure 13:
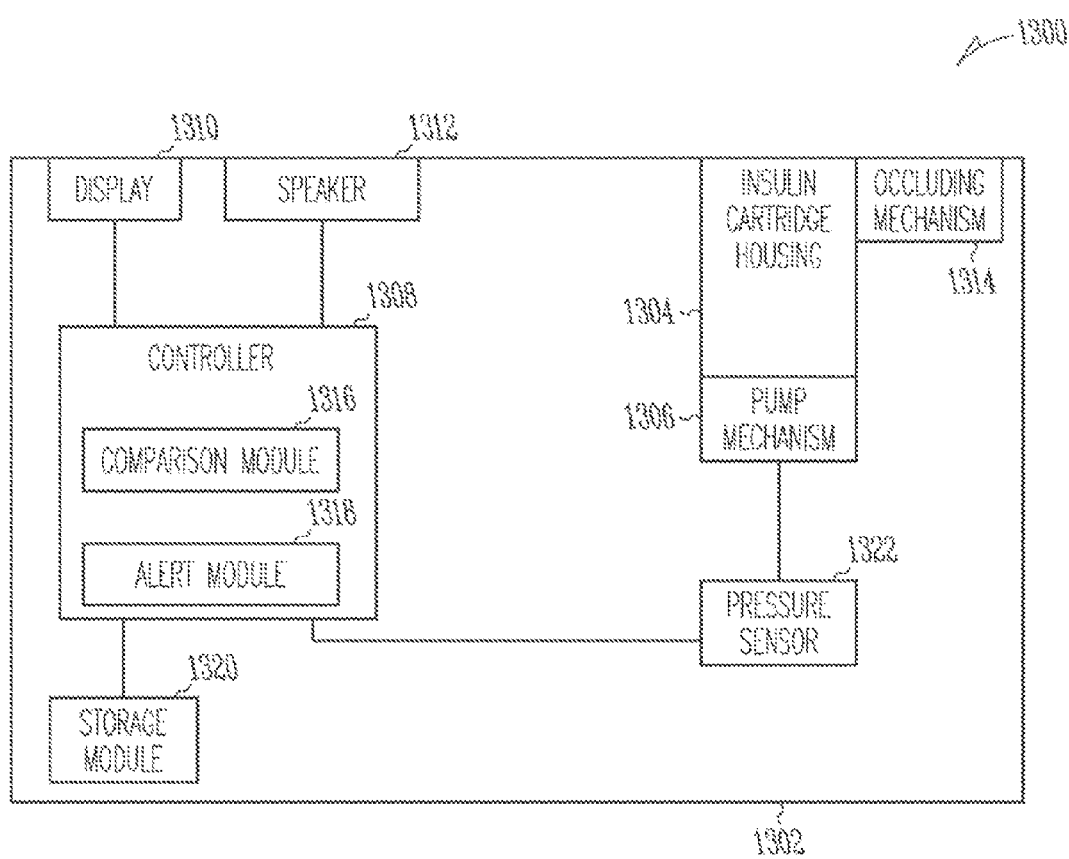
FIG. 13 is a schematic diagram of one example of a system for determining the presence of leaks in an insulin cartridge or an infusion tube set.

Another example of an insulin pump 1300 is shown in FIG. 13. As shown, the insulin pump 1300 includes an insulin pump housing 1302 containing an insulin cartridge housing 1304. A pump mechanism 1306 is coupled with the insulin cartridge housing 1304. As previously described, the pump mechanism 1306 is configured to move insulin out of an insulin cartridge coupled with the insulin cartridge housing 1304. For instance, the pump mechanism 1306 includes a plunger that is driven into the insulin cartridge within the cartridge housing 1304. The plunger is forces the insulin out of a discharge outlet of the insulin cartridge and into an infusion tube, such as infusion tubing 300, 302 previously shown in FIGS. 3A, B. A controller 1308 is coupled with the pump mechanism 1306 and is configured to operate the pump mechanism 1306 for dispensing insulin infusions as well as detecting leaks within the system of at least one of the insulin cartridge and a system of the insulin cartridge and the infusion tubing.

In another example, a display 1310 is coupled with the controller 1308. The display 1310 provides information to the user including alerts regarding the presence of leaks within the system of at least one of the insulin cartridge and a system of the insulin cartridge and the infusion tube. In yet another example, the insulin pump 1300 includes an audible output such as a speaker 1312 coupled with the insulin pump housing 1302. The speaker 1312 provides audible alerts to the user including but not limited to an alert that a leak is present in at least one of the insulin cartridge and the infusion tube, and instructions to change at least one of the insulin cartridge and the infusion tube.

A pressure sensor 1322 is coupled between the controller 1308 and the pump mechanism 1306. The pressure sensor 1322 is configured to measure pressures within at least one of the insulin cartridge and the system of the insulin cartridge in communication with the infusion tube. As previously described in other examples, an occluding mechanism 1314 is included for occluding at least one of the insulin cartridge and the infusion tube. Occlusion of one of the insulin cartridge and the infusion tube creates a sealed system allowing the pressure sensor to perform pressure measurements through use of the pump mechanism, for instance, by feedback information received from the pump mechanism 1306.

As previously described and shown in FIGS. 10 and 11, the pump mechanism 1306 in operation is actuated so a plunger is moved into the insulin cartridge housing 1304 a specified amount. Movement of the plunger into the insulin cartridge contained within the housing 1304, where at least one of the insulin cartridge and the infusion tube is occluded, generates a pressure within the system. Pressure is measured by the pressure sensor 1322 and communicated with the controller 1308. In another example, the pressure measurement is stored in a storage module 1320. At least two pressure measurements are measured by the pressure sensors 1322 over a period of time that the pump mechanism plunger 1306 is moved to a stationary position within the insulin cartridge housing 1304. The plunger is maintained at a specified position within the insulin cartridge, and in a sealed system without leaks pressure measurements over the period of time should be substantially identical.

The at least two pressure measurements taken by the pressure sensor 1322 over the period of time and at different times during that period are stored in the storage module 1320. The measurements are then compared at a comparison module 1316 within the controller 1308. Where the measurements are substantially the same over the period of time a determination is made that the system is not leaking. Where the second pressure measurement taken after the first measurement over the period of time is less than the first measurement a leak may be present in at least one of the cartridge and the infusion tube. The alert module 1318 thereafter provides an alert to the user, for instance, through the display 1310, the speaker 1312 and the like. In one example, the alert includes instructions to exchange at least one of the cartridge and the infusion tube including, but not limited to, visual and audio instructions.

Optionally, the operation of the controller 1308 to detect leaks within the system of at least one of the insulin cartridge and the infusion tube in combination with the insulin cartridge is performed automatically upon insertion of an insulin cartridge within the insulin cartridge 1304. In another example, the operation of the controller 1308 to detect leaks within the system is performed on an as needed basis according to user instructions, for instance, from the input module 104 shown in FIG. 4. For example, the user instructs the insulin pump 1300 to perform the necessary assessment where delivery of insulin is slow or non-existent.

Figure 14:
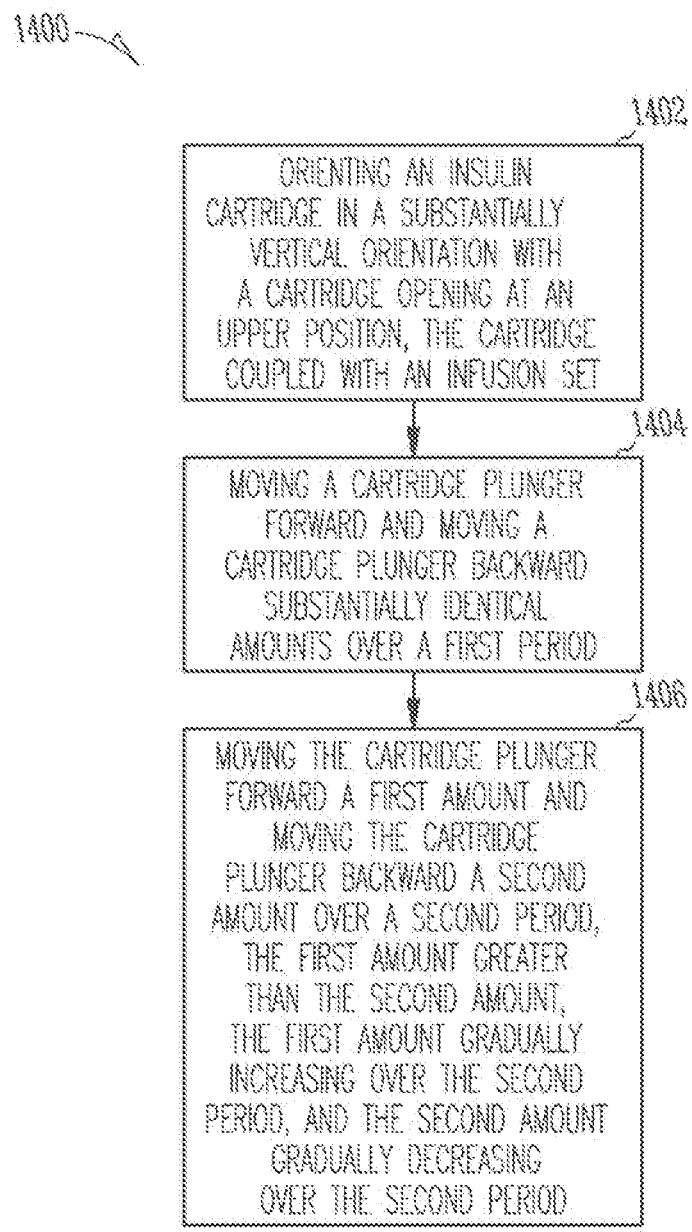
FIG. 14 is a block diagram showing one example of a method for removing air bubbles in an insulin cartridge.

One example of a method 1400 for removing air bubbles in an insulin cartridge is shown in FIG. 14. At 1402, an insulin cartridge is oriented in a substantially vertical fashion with a cartridge opening at an upward position (e.g., the infusion tube fitting 207 of the insulin cartridge 206 shown in FIGS. 2A, B). For example, the cartridge opening is at the top most portion of an insulin pump system such as the insulin pump 100, 200 shown in FIGS. 1A, B, 2A, B. The insulin cartridge is then coupled with an infusion set such as the infusion tubing 300, 302 shown in FIGS. 3A, B. The insulin cartridge is in communication with the infusion tube allowing insulin movement from the insulin cartridge through the infusion tube. As discussed below, the infusion tube 300, 302 serves as reservoir to receive insulin discharged from the insulin cartridge during a flushing operation to remove air bubbles from within the insulin cartridge.

The method 1400 includes a tube filling algorithm having at least two portions, an air bubble removing portion (described immediately below) and an air bubble and infusion tube filling portion (described below). At 1404, the method 1400 includes moving a cartridge plunger forward and moving the cartridge plunger backward substantially identical amounts over a first period. As described below, this backward and forward movement of the cartridge plunger acts to move the insulin through the cartridge in a reciprocating manner. The reciprocating motion of the insulin flow acts on air bubbles within the cartridge and moves air bubbles out of the insulin cartridge and into the infusion tube where the air bubbles may be discharged through the infusion tube discharge, such as luer fitting 145 shown FIGS. 3A, B. In another example, and further described below, the cartridge plunger is moved at one or more frequencies. Reciprocating movement of the cartridge plunger at one or more frequencies correspondingly moves the insulin within the insulin cartridge at one or more frequencies to change multiple insulin flow characteristics (velocity, pressure, turbulence and the like) to act on air bubbles with a variety of sizes and locations within the cartridge.

At 1406, the method 1400 includes moving the cartridge plunger forward a first amount and moving the cartridge backward a second amount over a second period. The first amount of forward cartridge plunger movement is greater than the second amount of reverse cartridge plunger movement. The first amount of the forward cartridge plunger movement gradually increases over the second period and the second amount of the reverse cartridge plunger movement gradually decreases over the second period. The gradual change of the forward and backward movement of the cartridge plunger correspondingly gradually fills the infusion tubing such as infusion tubing 300, 302 while continuing to discharge air bubbles out of the insulin cartridge. In one example, the movement of the cartridge plunger backward is fully eliminated in favor of forward movement of the cartridge plunger to allow filling of the infusion tubing and subsequent use of the insulin pump 100 for dispensing of insulin.

Several options for the method 1400 follow. In one example, the method 1400 further includes vibrating at least the insulin cartridge. As described below, the insulin pump such as the pump 100 includes a vibrating mechanism. The vibrating mechanism is configured to supplement the rapid forward and backward movement of the cartridge plunger to remove air bubbles within the insulin cartridge. In another example, moving the cartridge plunger forward and moving the cartridge plunger backward over at least one of the first and second periods is performed at one or more specified rates, such as one or more specified frequencies. For instance, the rate of forward and backward cartridge plunger movement is at a frequency greater than that of the incremental forward movement of the cartridge plunger during regular insulin infusing for basil and bolus infusions. The increased frequency of plunger movement assists in removing air bubbles from the insulin cartridge. In still another example, moving the cartridge forward and backward is performed at one or more specified rates including but not limited to the specified rates between around 10-100 hertz and the like. In yet another example, the method 1400 includes unsealing at least one of the insulin cartridge and the infusion set tubing prior to coupling of the insulin cartridge and infusion set tubing to allow communication therebetween during forward and backward movement of the cartridge plunger during at least the second period. As discussed above, communication between the insulin cartridge and the infusion set tubing allows for filling of the infusion set tubing while the insulin pump is cycling the cartridge plunger forward and backward to move air bubbles out of the insulin cartridge and into the infusion set tubing for eventual discharge out of the tubing.

Figure 15:
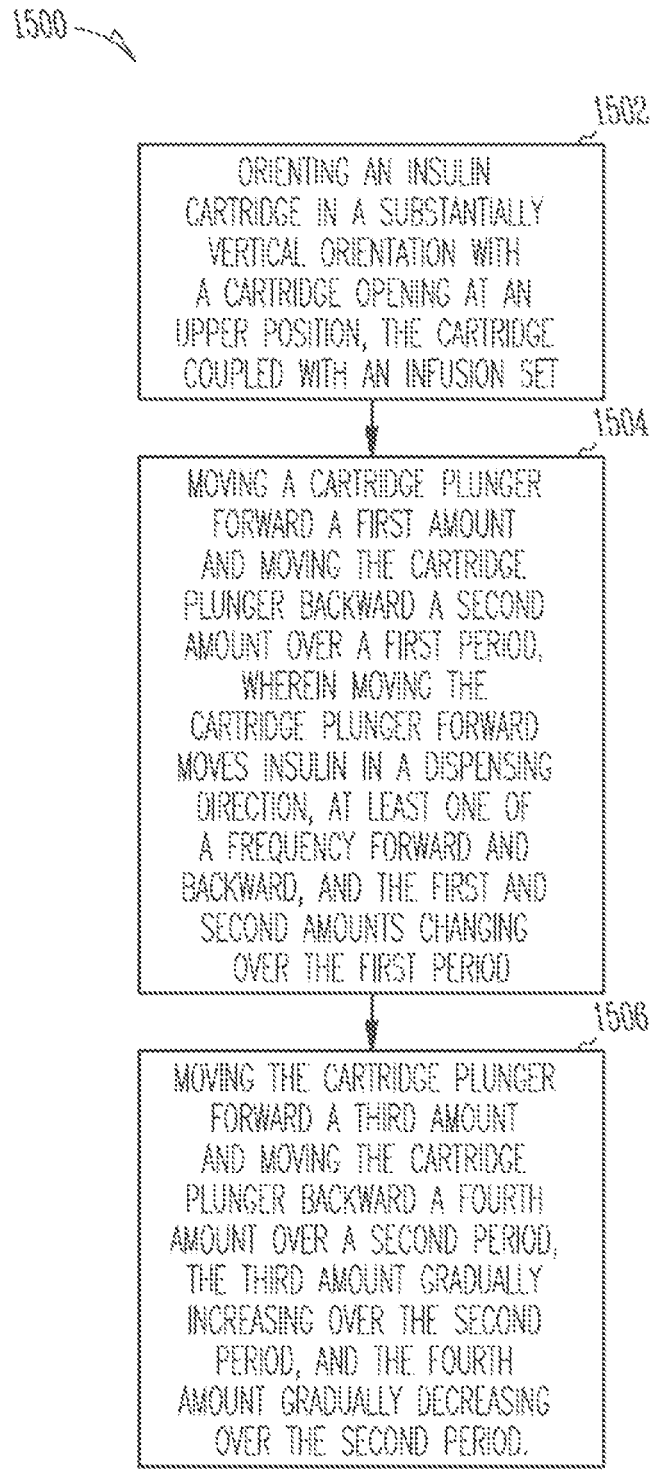
FIG. 15 is a block diagram showing another example of a method for removing air bubbles in an insulin cartridge.

Another example of a method 1500 for removing air bubbles in an insulin cartridge is shown in FIG. 15. At 1502, an insulin cartridge such as, insulin cartridge 206 shown in FIGS. 2A, B, is oriented in a substantially vertical orientation with a cartridge opening at an upward position. For example, the insulin cartridge is positioned with an insulin pump, such as the insulin pumps 100, 200 shown in FIGS. 1A, B, 2A, B. The insulin cartridge is open and coupled with an infusion set including infusion tubing, such as the infusion tubes 300, 302 shown in FIGS. 3A, B. As described below, coupling of the infusion set with the insulin cartridge allows for filling of the infusion tubing during removal of air bubbles within the insulin cartridge. As described below, the method 1500 thereby performs a dual function at the same time by filling the infusion tubing as well as removing air bubbles from the insulin cartridge.

The method 1500 includes a tube filling algorithm having at least two portions, an air bubble removing portion (described immediately below) and an air bubble and infusion tube filling portion (described further below). At 1504, a cartridge plunger, such as cartridge plunger 210 (FIGS. 2A, B) within the insulin pump is moved forward a first amount and backward a second amount over a first period of time. Moving the cartridge plunger forward moves the insulin within the insulin cartridge in a dispensing direction, for instance, through the infusion tubing 300, 302 (see FIGS. 3A, B). Backward movement of the cartridge plunger 210 moves the insulin in a direction reversed relative to the dispensing direction. At least one of a frequency of movement forward and backward, and first and second amounts of movement are changed over the first period. The frequency of reciprocal movement and the amount of reciprocal movement are changed over the first period to change a variety of flow characteristics within the insulin cartridge (e.g., velocity, pressure, turbulent flow, laminar flow and the like). The changing flow characteristics of the insulin act upon air bubbles within the insulin cartridge to move the air bubbles in the insulin cartridge toward an insulin cartridge opening and into the infusion tubing for eventual discharge through the infusion tubing outlet. In one example, the frequency of forward and backward cartridge plunger movement is changed according to a first schema over the first period. In another example, the first and second amounts of cartridge plunger movement are changed according to a second schema over the first period.

As described below, several options for the first schema change the frequency of reciprocating forward and backward cartridge plunger movement. In one example, the first schema for changing the rate of forward and backward movement of the cartridge plunger includes changing the frequency of the cartridge plunger movement in a random pattern over the first period. In one example, the insulin pump such as insulin pump 100 shown in FIGS. 1A, B, includes a memory having a catalog of plunger movement frequencies. The controller within the insulin pump randomly determines from this catalog what frequencies to use over the first period of time. Optionally, a plurality of frequencies are chosen over this first period of time to ensure the insulin has a variety of flow characteristics within the insulin cartridge to ensure movement of air bubbles out of the insulin cartridge. In another example, the controller of insulin pump 100 includes a random frequency generator that randomly generates frequencies that are subsequently used by the controller to adjust the frequency of cartridge plunger movement through the pump mechanism. In either case, where the frequencies of cartridge plunger movement are selected from a catalog within the controller or are generated within the controller the cartridge plunger is cycled forward and backward at a plurality of frequencies during the first period. For example, the cartridge plunger is cycled forward and backward at a first frequency during the first period. At a second span of time within the first period, the cartridge plunger is cycled forward and backward at a second frequency, and the second frequency is less than the first frequency. At a third span of time within the first period, the cartridge plunger is cycled forward and backward at a third frequency, and the third frequency is greater than the second frequency.

In yet another example, changing the frequency of forward and backward cartridge plunger movement over the first period includes changing the frequency over a range of frequencies during the first period. As previously described above, a variety of frequencies of cartridge plunger movement correspondingly creates a variety of flow characteristics within the insulin in the insulin cartridge. Similarly, by using a number of frequencies over a frequency range during the first period a corresponding plurality of flow characteristics are created within the insulin cartridge. The varied flow characteristics of the insulin generated by the change in frequency over the frequency range act on air bubbles of various sizes and at various locations within the insulin cartridge to ensure removal of air bubbles throughout the cartridge.

Alternatively or in addition to changing the frequency of cartridge plunger reciprocation, several options for changing the first and second amounts of cartridge plunger movement according to a second schema over the first time period are provided below. In one example, moving the cartridge plunger the first amount moves the cartridge plunger forward a specified distance in an insulin dispensing direction. Moving the cartridge plunger the second amount moves the cartridge plunger a specified amount backward. In one example, changing the first and second amounts of cartridge movements according to the second schema includes randomly changing the first and second amounts of cartridge plunger movement over the first period, for instance according to a catalog of frequencies that are randomly selected or a random frequency generator. Optionally, randomly changing the first and second amounts over the first period includes constraining the first amount (forward cartridge movement) to be the same or less than the second amount. Constraining forward movement of the cartridge plunger ensures that over the first period the reciprocating movement of the cartridge plunger does not dispense insulin through the infusion tubing. Insulin is thereby not undesirably dispensed and is instead conserved for later filling operations and intended infusions.

In yet another example, the cartridge plunger is moved a first forward amount and a second backward amount according to a range of cartridge movement values within the controller of the insulin pump 100. For example, the cartridge plunger is moved through a range of cartridge plunger movements from no (zero) movement of the cartridge plunger to full movement of the cartridge plunger (maximum mechanical travel) within the insulin pump. In yet another example, the cartridge plunger movement amounts forward and backward are limited to ensure the insulin within the insulin cartridge is at least retained within one of the insulin cartridge and the infusion tube without undesirable dispensing of the insulin through the infusion tube prior to removal of air bubbles from the insulin cartridge.

At 1506, the method 1500 includes moving the cartridge plunger forward a third amount and moving the cartridge plunger backward a fourth amount over a second period of time. The third amount of forward cartridge plunger movement gradually increases over the second period and the fourth amount of backward cartridge plunger movement gradually decreases over the second period. The gradual change of the reciprocating cartridge plunger movement toward solely forward movement ends cycling of the cartridge plunger for air bubble removal. The backward movement of the cartridge plunger gradually ceases in favor of forward movement of the cartridge plunger. As the reciprocating action gradually shifts to forward cartridge plunger movement the cartridge plunger of the insulin pump moves the insulin out of the insulin cartridge and into the infusion tube to fill the infusion tube for infusion to a user.

As described above, the air bubble removal methods such as methods 1400, 1500 remove air bubbles from an insulin cartridge after its installation within the insulin pump and prior to dispensing of insulin to the user through the infusion tube. The methods 1400, 1500 provide a dual function of removing air bubbles as well as filling the infusion tube prior to insulin infusion to the user. In one example, the methods 1400, 1500 are performed automatically upon installation of a new insulin cartridge within the insulin pump. Automatic performance of the air bubble removal methods provides a measure of confidence that the insulin cartridges are without air when insulin infusion begins. Additionally, the user is able to concentrate on other activities while the insulin pump system removes the air bubbles and fills the infusion tube prior to standard insulin infusing from the pump. Further, filling of the infusion tube is performed as part of the air bubble removal method thereby consolidating both activities to save time between installation of the insulin cartridge and insulin infusion. Further still, providing a plurality of frequencies for cartridge plunger reciprocation and changing the amount of cartridge plunger movement ensures a the insulin in the cartridge experiences a variety of flow characteristics (e.g., velocities, pressures, turbulent flow, laminar flow and the like) to remove air bubbles of multiple sizes and having multiple locations within the insulin cartridge.

Figure 16:
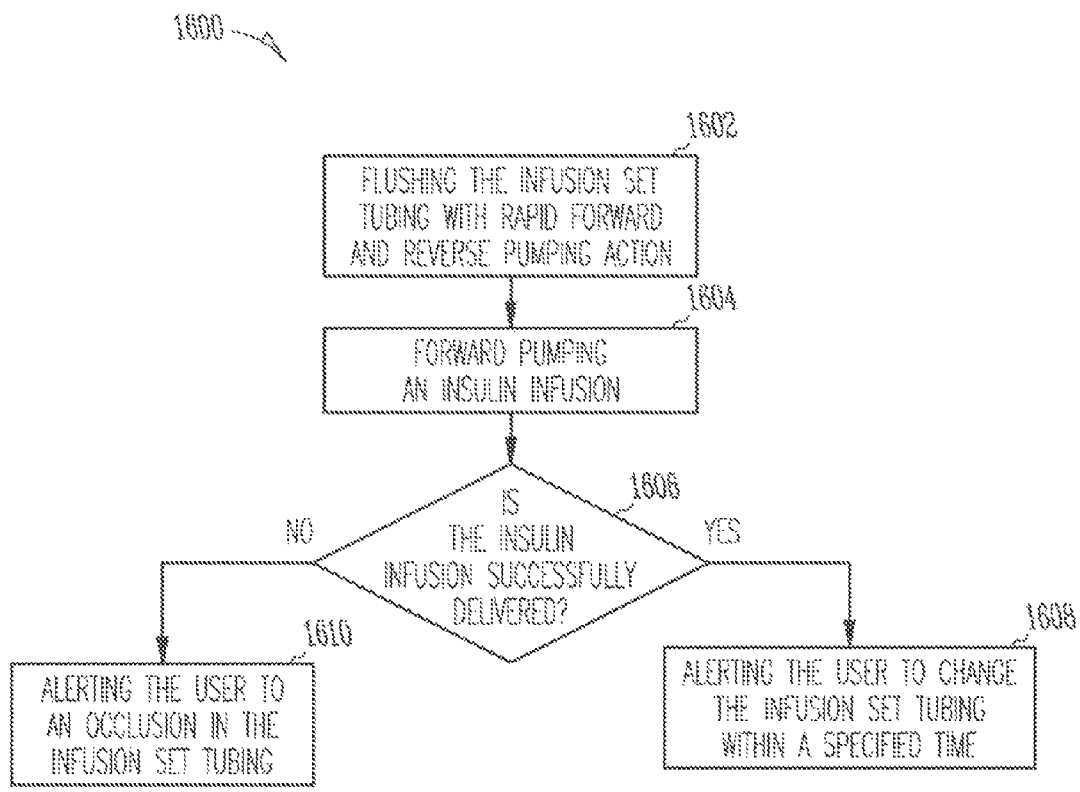
FIG. 16 is a flowchart showing one example of a method for clearing occlusions in an infusion set tubing.

Referring now to FIG. 16, a method 1600 for clearing occlusions within infusion tubes is shown. At 1602, where an occlusion is present within the infusion tubing the infusion tubing is flushed with rapid forward and reverse pumping action movements. For instance, a pump mechanism, such as cartridge plunger 210 (FIGS. 2A, B) is rapidly cycled backwards and forwards to move the insulin within the infusion tubing to flush an occlusion out of the tubing. In one example, the insulin pump is cycled at various frequencies to provide a rapid change of pressures to the insulin to dislodge the occlusion from the infusion set tubing. In still another example, the controller of the insulin pump adjusts the backwards and forwards movement of the cartridge plunger to provide a variety of pressures to dislodge the occlusion from the infusion tubing.

After flushing of the infusion set tubing at 1604 the insulin pump attempts to infuse the insulin infusion through the infusion tubing, for instance, by forward pumping the insulin through the infusion tubing. At 1606, the method 1600 includes determining whether the insulin infusion was successfully delivered through the infusion tubing. For example, feedback from the pump mechanism such as pump mechanisms 208, 402 shown in FIGS. 2A, B, 4 is used by a pressure detection module 406 (also shown in FIG. 4). If the pressure detection module 406 detects that there is a pressure build up within the insulin cartridge beyond a specified pressure threshold a determination is made that the occlusion remains within the infusion set tubing. If the infusion is successfully delivered through the infusion tubing, indicated by pressure measurements taken within the insulin cartridge being below a specified pressure threshold, a controller 404 within the insulin pump proceeds with regular operation of the insulin pump.

At 1608, the user is alerted to change the infusion set tubing within a specified time where the insulin infusion is successfully delivered after the flushing action with the insulin pump (step 1602). The alert indicates to the user that an inclusion was successfully cleared from the infusion set tubing and provides that the current infusion tubing should be exchanged for new infusion tubing to reduce the likelihood of additional occlusions within the existing infusion tubing. In one example, the specified time includes one hour, twelve hours, twenty-four, forty-eight hours and the like. Optionally, the specified time for the alert is based upon a pressure detected within the insulin cartridge prior to flushing of the occlusion out of the infusion set tubing. For example, where the pressure measurement is high relative to the specified pressure indicating a full occlusion of the infusion set tubing the corresponding specified time for the alert is set to a minimal time to ensure that the user quickly exchanges the current infusion set tubing for a new infusion set tubing to avoid the possibility of a complete occlusion of the existing infusion set tubing. Where the pressure measurement within the insulin cartridge prior to flushing of the inclusion is above but near the specified pressure threshold indicating a partial occlusion of the infusion tubing the specified time in the alert to the user is correspondingly larger because the occlusion is partial or easily dislodged (e.g., insulin is continuing to be administered to the user despite the partial occlusion).

At 1610, an alert is provided to the user that an occlusion is in the infusion set tubing. The alert includes additional information that an attempt has been made to move the occlusion out of the infusion tubing through unsuccessful flushing action of the insulin pump. The alert informs the user that an immediate change of the infusion tubing is needed to continue operation of the insulin pump. In yet another example, the alert informing the user of an occlusion within the infusion set tubing includes a prompt allowing the user to perform another flushing cycle to attempt to remove the occlusion.

Several options for the method 1600 follow. In one example, flushing the infusion set tubing includes forward pumping and reverse pumping at a plurality frequencies within a frequency range over a period of time. As previously discussed above, cycling the insulin pump mechanism at a variety of frequencies provides changes the flow characteristics in the insulin within the insulin cartridge and the infusion set tubing. The changes in flow characteristics impose a variety of cyclical forces (e.g., forward and backward forces with changing values) against the occlusion to dislodge the occlusion from within the insulin infusion tubing. In yet another example, the infusion set tubing is flushed with rapid forward and reverse pumping action at a plurality of frequencies, for example, a plurality of frequencies stored within a storage module, randomly generated by the insulin pump controller and the like.

In yet another example, flushing the infusion set tubing includes forward pumping a first amount and reverse pumping a second amount where the forward pumping amount is equal to or less than the second amount of reverse pumping. Constraining the forward pumping amount to less than the reverse pumping amount insures that pressurized insulin used to remove the occlusion is not violently forced through the infusion set tubing if the occlusion breaks loose within the infusion set tubing. Unintended insulin infusions are thereby avoided. Optionally, the infusion set tubing is flushed so that the reverse pumping second amount is less than the intended bolus delivery that was interrupted by the occlusion. For instance, if the intended bolus delivery was one unit of insulin, the plunger is reversed a distance corresponding to the one unit of insulin.

In still another example, flushing the infusion set tubing includes forward pumping the first amount and reverse pumping the second amount where the first amount and the second amount change over the first period. Changing the amount of pump movement during the flushing action provides a variety of cyclical forces to the occlusion by way of the pressurized insulin. The various forces dislodge the occlusion and flush it down the infusion set tubing. Optionally, the first forward pumping amount and the second reverse pumping amount are changed according to a scheme within the insulin pump controller. In another example, the insulin pump controller includes a generator that randomly generates the first forward pumping and second reverse pumping amounts.

Figure 17:
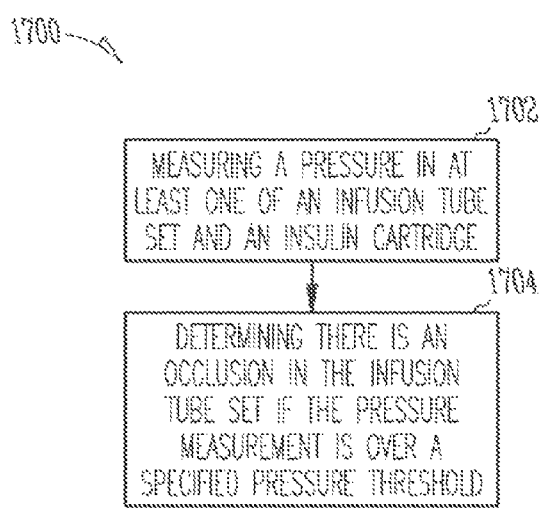
FIG. 17 is a flowchart showing one example of a method for detecting an occlusion in an infusion set tubing.

Referring now to FIG. 17, method 1700 for detecting the presence of an occlusion within an infusion set tubing is shown. At 1702, a pressure is measured in at least one of the infusion tube set and an insulin cartridge. For instance, as shown in FIG. 4, a pressure detection module 406 is coupled between a pump mechanism 402 and a controller 404 within an insulin pump 100. In one example, the pressure detection module 406 detects the pressure within the insulin cartridge according to feedback from the pump mechanism 402. Where an occlusion is present within the insulin infusion tubing the pump mechanism provides corresponding feedback and the pressure detection module equates the detected feedback to a rise in pressure. At 1704, a determination is made that an occlusion is present if the pressure measurement is over a specified pressure threshold. Where an occlusion is detected based on the comparison of the pressure measurement with the specified pressure threshold, the controller 404 performs the method 1600 for removing the occlusion from the infusion tubing. Optionally, the method 1700 is performed after the method 1600 where an occlusion has been flushed from the infusion set tubing. Method 1700 performs additional pressure measurements of the infusion set tubing to indicate whether or not the occlusion has been successfully removed by the flushing action of the insulin pump as described in method 1600.

FIG. 18 shows one example of a method 1800 for reducing the pressure build up within the system of the insulin cartridge and the infusion tubing after a flushing action of the pump mechanism and before an attempted infusion of the insulin, such as an insulin infusion 1604 shown in FIG. 16. At 1802, the pumping action is reversed prior to forward pumping of the insulin infusion. The reverse pumping action within the system of the insulin cartridge in the infusion set tubing decreases the pressure within the system thereby minimizing the chance that any residual pressure from the flushing action (step 1602) is combined with pressure built from forward pumping action used to move the insulin infusion forward through the infusion set tubing to the user. For instance, if an occlusion is still present within the infusion set tubing after the flushing action any residual pressure from the flushing movement of the pump mechanism would be added within the forward pumping action of the pump mechanism intended for movement of the insulin infusion toward the user. By reversing the pumping action prior to forward movement of the pump mechanism for the insulin infusion the only pressure developed within the system of the insulin cartridge and the infusion set tubing is that from the forward pumping action that is intended to infuse the insulin to the user if an occlusion still remains with the infusion set tubing the occlusion should not be violently dislodged by the forward pumping action for the insulin infusion because any residual pressure from the flushing action has been eliminated by the reverse pumping movement.

FIG. 19 of method 1900 is shown for controlling a pressure within a system of the insulin cartridge in the infusion tubing where an occlusion has been detected within the infusion tubing. At 1902 the insulin pump attempts to deliver an insulin infusion to the user as previously described above, in one example, pressure measurements are used to determine the presence of an occlusion within the infusion set tubing. At 1904, the insulin pump action is reversed specified amount if an occlusion is detected. By reversing the insulin pump action prior to a flushing action of the insulin pump (see step 1602 in FIG. 16) the subsequent flushing action occurs within a system that is not already pressurized. Flushing action within this pressure minimized environment should thereby not violently dislodge the occlusion and provide an undesired insulin infusion rapidly to the user.

Referring now to FIG. 20, one example of an insulin pump 2000 is shown. Insulin pump 2000 includes an insulin pump housing 2002, including a pump mechanism 2004 and an insulin cartridge housing 2006. As previously described in another example, the insulin cartridge housing 2006 is sized and shaped to receive an insulin cartridge and the pump mechanism 2004 moves the insulin out of the insulin cartridge and into an infusion set tubing such as infusion tubes 300, 302 shown in FIGS. 3A, B. In one example, the pump mechanism 2004 includes a cartridge plunger (e.g., a piston) sized and shaped to move into the insulin cartridge and move insulin out the cartridge through the infusion tube. In another example, the pump mechanism 2004 includes a metering pump including, but not limited to, a diaphragm pump, peristaltic pump and the like. A controller 2008 is coupled with the pump mechanism 2004. The controller 2008 provides instructions for actuation of the pump mechanism 2004 to move insulin through the system of the insulin cartridge and infusion tube in addition to removing air bubbles as previously described in FIGS. 14 and 15 (methods 1400, 1500).

Controller 2008 includes an infusion tube filling algorithm module 2010. The infusion tube filling algorithm module 2010 includes a series of protocols intended to remove air bubbles within the insulin cartridge and infuse insulin into the infusion tube prior to operation of the insulin pump for bolus and basal infusions.

An air bubble removing module 2012 is contained within the infusion tube filling algorithm module 2010. The air bubble removing module 2012 instructs the pump mechanism to remove air bubbles within the insulin cartridge, for instance, as previously described in the methods 1400, 1500. In one example, the air bubble removing module 2010 adjusts the amount of pump action, for instance, the movement amount of the cartridge plunger forward and backward. Adjusting the amount of forward and backward movement of the pump mechanism correspondingly provides varying flow characteristics (e.g., velocity, turbulent flow, laminar flow and the like) to insulin within the insulin cartridge. The moving insulin experiencing these varied flow characteristics acts on air bubbles of different sizes in different locations within the insulin cartridge to move the air bubbles out of the insulin cartridge and into the infusion tube for eventual discharge to the infusion tube outlet. Similarly, in another example, the air bubble removing module 2012 instructs the pump mechanism 2004 to change the frequency of reciprocating pumping action. The pump mechanism 2004 thereby cycles movement of insulin within the insulin cartridge at one or more frequencies to stir the insulin within the insulin cartridge and thereby force air bubbles out of the cartridge. In a similar manner to changes of the amount of pump action, changes to the frequency of the pump action provide a variety of flow characteristics to the insulin including, but not limited to changes in velocity, turbulent flow, laminar flow and the like. Insulin experiencing these changing flow characteristics acts on air bubbles of various sizes and at various locations within the insulin cartridge to maximize the removal of air bubbles from the insulin cartridge.

The infusion tube filling algorithm module 2010 further includes an infusion tube filling module 2014. After the pump mechanism is operated through a first step to remove air bubbles from the insulin cartridge, the pump mechanism 2004 gradually moves insulin forward through the infusion tubing, and through reverse movement of the pump mechanism, draws insulin back into the insulin cartridge from the infusion tubing with a net forward movement of insulin through the infusion tubing. Forward and reverse movement of insulin within the insulin cartridge continues to remove air bubbles from the insulin cartridge. At the same time, insulin is gradually moved into the insulin infusion tubing (See FIGS. 2A, B) to prepare the insulin pump and the infusion tubing for normal operation including basal and bolus infusions. For example, in methods 1400, 1500 the cartridge plunger is moved forward and backward in specified amounts. The forward specified amount is gradually increase over a period of time while the backward specified amount is gradually decreased. The infusion tube is thereby gradually filled as the insulin within the insulin cartridge is moved progressively forward relative to gradual reductions in reverse movement of the insulin. The insulin pump 2000 and infusion tubing are thereby immediately ready for infusion of insulin to the user after performing the air bubble removing methods of the infusion tube filling algorithm module 2010 (e.g., air bubble removal module 2012 and infusion tube filling module 2014).

As described above, the air bubble removing module 2012 of the infusion tube filling algorithm module 2010 is configured to remove air bubbles from the insulin cartridge within the insulin cartridge housing 2006. The air bubble removing module 2012 operates the pump mechanism specified amounts forward and backward and at specified frequencies to remove air bubbles from the insulin cartridge. The air bubble removing module 2012 operates the pump mechanism to achieve a zero net insulin delivery prior to operation of the infusion tube filling module 2014. For example, the air bubble removing module 2012 moves the cartridge plunger a first forward infusing amount that is less than or equal to a backward reverse amount. Constraining forward infusing movements of the cartridge plunger this way substantially prevents insulin delivery during operation of the pump mechanism 2004 according to the air bubble removing module 2012.

In another example, the air bubble removing module 2012 is configured to operate the pump mechanism 2004 to move the cartridge plunger forward and backward in different amounts over a period of time. The forward infusion movement amounts and backward reversing movement amounts of the cartridge plunger are changed over the period of time. As described above, this applies a variety of flow characteristic to the insulin within the insulin cartridge and maximizes removal of a variety of air bubble sizes located at various locations within the insulin cartridge. In still another example, the air bubble removing module 2012 is configured to randomly change the forward infusion movements and backward reversing movements of the pump mechanism over a period of time.

In another example, the air bubble removing module 2012 is configured to operate the pump mechanism 2004 at one or more specified frequencies over a period of time. For example, the air bubble removing module 2012 reciprocates the cartridge plunger forward and backward at random frequencies over a period of time. In another example, the air bubble removing module 2012 operates the pump mechanism 2004 to move the cartridge plunger forward and backward at a plurality frequency within a frequency range over a period of time. Movement of the cartridge plunger forward and backward at a variety of frequencies including, but not limited to, random specified frequencies, and frequencies within a frequency range ensures a variety of flow characteristics are provided to the insulin. Air bubbles within the insulin cartridge are thereby subject to a variety of forces applied in various directions. For instance, air bubbles within the insulin cartridge are subject to turbulent and laminar flow having a variety of velocities that act upon the air bubbles to remove the air bubbles from the insulin cartridge.

Optionally, the insulin pump 2000 further includes, a vibrating mechanism 2016, as shown in FIG. 20. In one example, the vibrating mechanism 2016 is positioned adjacent to the insulin cartridge housing 2006. The vibrating mechanism 2016 is operated by the controller 2008 in combination with the infusion tube filling algorithm 2010 to remove air bubbles from the insulin cartridge housed within the insulin cartridge housing 2006. The vibrating mechanism 2016 thereby cooperates with the infusion tube filling algorithm and assists the algorithm 2010 with removal of air bubbles from the insulin cartridge.

Figure 21:
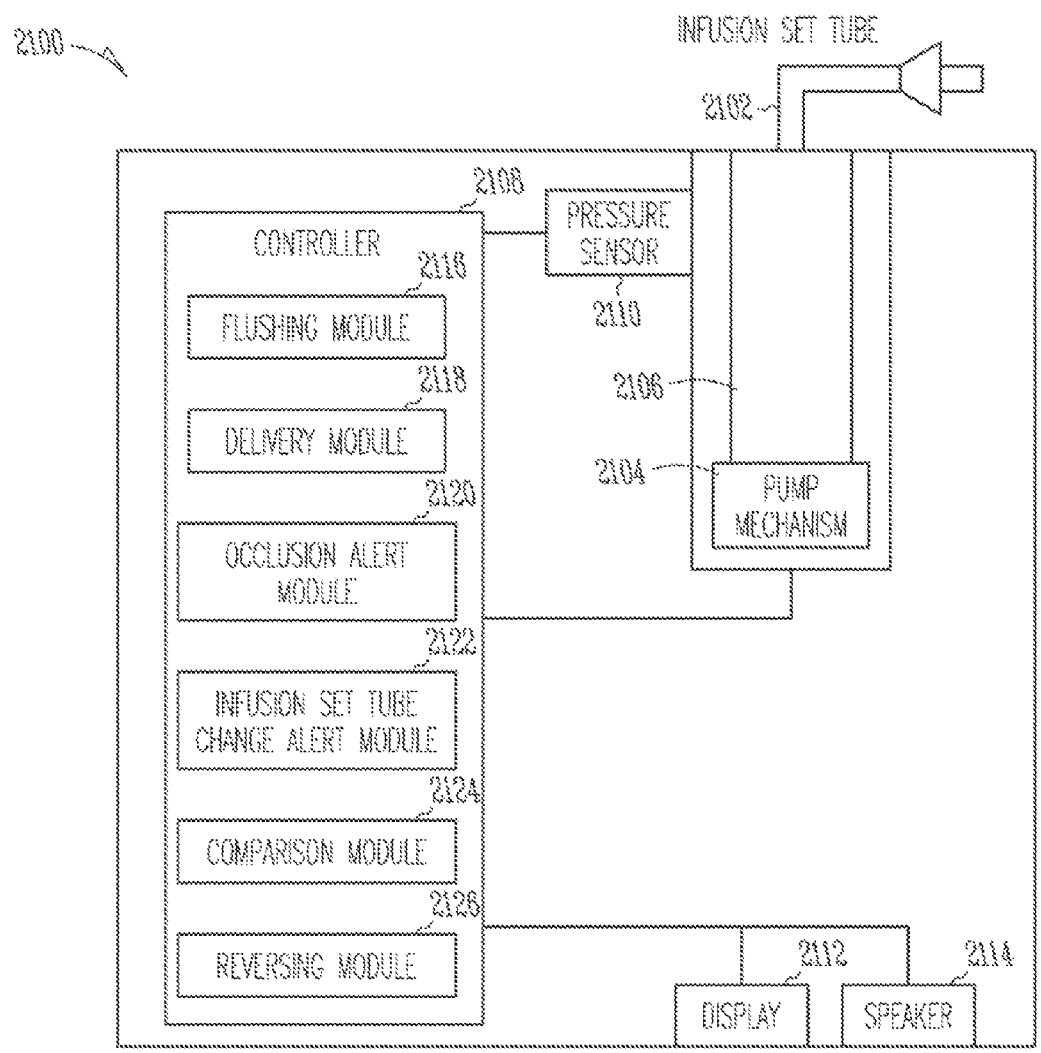
FIG. 21 is a schematic diagram of one example of a system for clearing occlusions in an infusion set tubing.

Another example of an insulin pump 2100 is shown in FIG. 21. Pump 2100 includes a pump mechanism 2104 coupled with an insulin cartridge housing 2106. As shown in FIG. 21, an infusion set tube 2102 extends away from the insulin pump 2100. The infusion set tube 2102 is coupled with the insulin cartridge (e.g., insulin cartridge 206 shown in FIGS. 2A, B) exposed within the insulin cartridge housing 2106. A controller 2108 is coupled with the pump mechanism 2104 and controls operation of the pump mechanism including basal and bolus infusions as well as flushing protocols to remove occlusions within the infusion set tube 2102.

In one example, a pressure sensor 2110 is coupled with at least one of the pump mechanism 2104 and insulin cartridge housing 2106. The pressure sensor 2110 is configured to detect pressure within at least one of the insulin cartridge and the system of the insulin cartridge and infusion set tube. The pressure sensor 2110, in one example, includes a pressure sensor mounted along a peripheral surface of the insulin cartridge housing 2106 such as, but not limited to, a piezoelectric sensor, strain gauge and the like. In another example, the pressure sensor 2110 is coupled with the pump mechanism 2104 and receives feedback information from the pump mechanism. The pressure sensor transmits the feedback information in the form of a corresponding pressure measurement to the controller 2108 for use by the controller modules to deliver insulin and flush occlusions from the infusion set tube 2102. Controller 2108 is further coupled with at least one output including a display 2112, a speaker 2114, and the like. In another example, controller 2108 is coupled with another output including a vibratory mechanism.

Referring again to FIG. 21, the controller 2108 includes a variety of modules configured to dislodge occlusions formed within the infusion set tube 2102. A flushing module 2116 is configured to operate the pump mechanism 2104 in a cyclical fashion to provide alternating forward and reverse movements of insulin within the insulin cartridge and infusion set tube 2102 to dislodge the occlusion within the infusion set tube. Flushing module 2116 provides, in one example, a rapid forward and reverse movement of the pump mechanism 2104.

As previously described, this rapid cyclical movement of the pump mechanism 2104 provides alternating pressure and vacuum on the occlusion within the infusion set tube 2102 helping to dislodge the occlusion from the infusion set tube. The delivery module 2118 within the controller 2108 is configured to deliver insulin infusions after the rapid forward and reverse flushing action. If the pump mechanism 2104 is unable to deliver the insulin infusion after operation of the flushing module 2116 the occlusion alert module 2120 within the controller 2108 is configured to alert the user to an occlusion in the infusion set tube 2102. If the pump mechanism 2104 is able to deliver the insulin infusion as instructed by the delivery module 2118 an alert is sent according to the infusion set tube change alert module 2122 advising the user to change the infusion set tube within a specified time. In another example, the insulin pump 2100 further includes a comparison module 2124. As further described below, the comparison module 2124 is configured to compare pressure measurements from the pressure sensor 2110 against specified pressure thresholds to assess the presence of occlusions within the infusion set tube 2102.

As previously described in FIG. 16 with method 1600 a pump mechanism, such as pump mechanism 2104, is reciprocally operated to provide forward and backward movement of insulin within the insulin cartridge and corresponding movement of insulin through the infusion set tube 2102 to dislodge occlusions within the infusion set tube. In one example, one or more frequencies of reciprocating movement of the pump mechanism 2104 are used to provide a variety of flow characteristics to the insulin and corresponding alternating pressure and vacuum forces on the occlusion. Rapid cycling of the pump mechanism 2104 applies pressure and a vacuum to the occlusion at one or more frequencies to dislodge the occlusion. For instance, the flushing module 2116 is configured to operate the pump mechanism 2104 to provide rapid forward and reverse pumping action at a plurality of frequencies. In another example, the plurality of frequencies are chosen from a range of frequencies stored within a controller 2108. In still another example, the flushing module 2116 operates the pump mechanism 2104 through the range of frequencies. The frequency of pump mechanism reciprocation thereby gradually changes from a first frequency within the frequency range through intermediate frequencies in the frequency range to a second frequency at the other end of the frequency range. In yet another example, the flushing module 2116 operates the pump mechanism 2104 at one or more frequencies where the frequencies are selected randomly from a memory within the controller 2108 or generated randomly by the controller 2108.

In another example, the flushing module 2116 is configured to operate the pump mechanism 2104 to provide the rapid forward and reverse pumping action including, for example, a first forward pumping action and a second reverse pumping action. The flushing module 2116 adjusts the first amount of the forward pumping action and the second amount of the reverse pumping action. The flushing module 2116 constrains the first amount of forward pumping action to be less than or equal to the second amount of reverse pumping action. Unintended dispensing of insulin from the insulin cartridge is thereby precluded through the infusion set tube 2102 while the flushing action of the flushing module 2116 is carried out. In another example, the first amount of forward pumping action and second amount of reverse pumping action are changed over a first period. In one option, the first amount and second amount are changed independently relative to each other. In another option, the first and second amounts are changed corresponding to each other. For example, as the second amount of the reverse pumping action is increased the first amount of the forward pumping action is correspondingly increased. Flushing module 2116 changes the first and second amounts of forward and reverse pumping action according to at least one scheme including but not limited to a random scheme, a preprogrammed scheme of alternating first and second amounts for forwarding and reverse pumping action, a range of first forward pumping amounts and second reverse pumping amounts that gradually change throughout the range, and the like.

As described above, the pressure sensor 2110 is configured to measure an insulin pressure within at least one of the fusion set tube 2102 and the insulin cartridge within the insulin cartridge housing 2106. The comparison module 2124 within the controller 2108 is configured to compare the measured insulin pressure from the pressure sensor 2110 with at least one specified pressure contained within the controller 2108, for instance, within a memory within the controller. An alert is sent to the user by the occlusion alert module 2120 if the insulin pressure measured by the pressure sensor 2110 is greater than at least one of the specified pressures within the controller 2108. In one example, the pressure sensor 2110 cooperates with the controller 2108 and the comparison module 2120 to determine whether or not an occlusion previously detected in the infusion set tube 2102 and acted upon by way of the flushing module 2116 has been dislodged from infusion set tube. After the flushing module 2116 operates the pump mechanism 2104 to dislodge the occlusion from the infusion set tube 2102, pressure measurements are taken by the pressure sensor 2110 and compared within the comparison module 2124 to determine whether or not the occlusion has been successfully removed from the infusion set tube 2102. If the pressure continues to be above the specified pressure threshold the occlusion module 2120 informs the user that the occlusion has not been cleared by the flushing module 2116. Optionally, the occlusion module 2120 instructs the user to first inspect the infusion tube for kinks or knots, and if none are found to immediately change out the infusion set tube 2102 to insure continuous operation of the insulin pump 2100.

In still another example, the pressure sensor 2110 takes pressure measurements from the system of the insulin cartridge and the infusion set tube 2102 on a continuous basis during normal operation of the insulin pump 2100. In one option, if at least one of the pressure measurements from the pressure sensor 2110 exceeds the specified pressure threshold the comparison module 2124 communicates with the flushing module 2116, and the flushing module 2116 instructs the pump mechanism 2104 to begin a flushing operation of the occlusion set tube. In another option, if the plurality of pressure measurements from the pressure sensor 2110 taken over a specified period of time exceeds the specified pressure threshold the comparison module 2124 communicates with the flushing module 2116. Flushing module 2116 operates the pump mechanism 2104 to begin flushing operations of the infusion set tube 2102. For example, if three or more pressure measurements over a three minute period from the pressure sensor 2110 exceed the specified pressure threshold the flushing module 2116 operates the pump mechanism 2104 to dislodge the occlusion from the infusion set tube 2102. That is to say three or more pressure measurements that are above the specified pressure threshold over the period of time indicates that an occlusion is present in the infusion set tube 2102. Using multiple pressure measurements to confirm the presence of an occlusion within the infusion tube 2102 provides additional confidence that the infusion set tube 2102 has an occlusion. In yet another option, the flushing module 2116 operates the pump mechanism 2104 to flush occlusions if three out of the five previous pressure measurements from the pressure sensor 2110 exceed a specified pressure threshold.

The controller 2108 includes, in another example, a reversing module 2126. The reversing module 2126 is configured to reverse a previous insulin delivery pump action prior to the flushing module 2116 operating the pump mechanism 2104 to provide the rapid forward and reverse pumping action. The reverse module 2126 thereby operates the pump mechanism 2104 prior to operation of the pump mechanism by of the flushing module 2116. The reversing module 2126 eliminates residual pressure provided by the pump mechanism 2104 in attempting to move the insulin through the infusion set tube 2102 prior to detection of the occlusion by the pressure sensor 2110. The reversing module 2126 thereby substantially prevents a buildup of pressure within the insulin cartridge and the infusion set tube 2102 during operation of the pump mechanism 2104 according to the protocols of the flushing module 2116. A violent dislodgement of an occlusion within the infusion set tube 2102 and an unintended infusion of insulin from the infusion set tube is thereby prevented.

In another option, the reversing module 2126 operates on the pump mechanism 2104 after the flushing module 2116 operates the pump mechanism 2104 to flush the occlusion out of the infusion set tube 2102. Operation of the reversing module 2126 after operation of the flushing module 2116 eliminates residual pressure and thereby substantially prevents the addition of residual pressure from the reciprocal flushing movement to an insulin infusion thereafter. Any residual pressure generated by the pump mechanism 2104 according to flushing instructions from the flushing module 2116 is thereby not added to the pressure generated by the pump mechanism 2104 according to the insulin infusion after the flushing operation.

CONCLUSION

The above described systems and methods address the inclusion of air bubbles, occlusions and leaks within an insulin pump system. The systems and methods are configured to detect the presence of air bubbles and leaks within the system of the insulin cartridge and infusion tube, for instance, through pressure measurements. Detection of air bubbles and leaks allows for removal of the air bubbles or replacement of the insulin cartridge or infusion tube containing the leak. As described above, the systems and methods are further configured to remove air bubbles from the insulin cartridge and the infusion tube to ensure consistent bubble free delivery of insulin to the user. In one example, the systems and methods for detecting the presence of air bubbles are used in combination with the systems and methods for removing air bubbles. For instance, the insulin pump detects the presence of air bubbles within at least one of the infusion tube and the insulin cartridge. Upon detecting air bubbles, the insulin pump removes air bubbles from the system by operating the pump mechanism (automatically or with user prompts) according to at least one of the above described air bubble removal algorithms. Alternatively, where air bubbles are present in the infusion tube, the user is alerted to the presence of infusion tube bubbles and is prompted to enter the locations and lengths of the bubbles for monitoring and adjustment of infusion volume.

Moreover, the systems and methods are configured to detect the presence of occlusions within the infusion tube, for example, through pressure measurements, and attempt to flush the occlusions out of the infusion tube. Optionally, the system or method automatically attempts to remove the occlusions. In another option, the system or method removes the occlusions according to instructions received from the user.

The systems and methods for detecting and removing occlusions are used in combination with the systems and methods for detecting and removing air bubbles and detecting leaks, in another example. That is to say, each of the systems and methods are combinable within a single insulin delivery device to detect a variety of issues within the insulin cartridge and the infusion tube and attempt to automatically (or with user prompts) remedy those issues.

The systems and methods for adjusting the insulin infusion volume based on the presence of air in an infusion tube determines an adjusted (composite) insulin infusion volume by adding the air bubble volume with the desired insulin infusion volume. The adjusted insulin infusion volume thereby ensures that a proper amount of the insulin infusion is actually delivered to the user despite the presence of air bubbles within the infusion tube. Alternatively, the systems and methods monitor the location of the air bubble and alert the user to the presence of the air bubble as it nears the infusion site of the user. The user is then conveniently provided with an option to disconnect the infusion tube from the infusion site and allow the insulin pump to cycle out the air bubble avoiding possible complications, such as an air embolism. The user then reconnects the infusion tube at the infusion site to continue the insulin infusion. Moreover, because the systems and methods described above are configured to monitor the location of air bubbles in the infusion tube as the air bubbles move with insulin through the infusion tube, the user is free to concentrate on other activities without having to observe the air bubble location until immediately before its inclusion in a delivered insulin infusion.

The systems and methods for detecting the presence of air and leaks in at least one of the insulin cartridge and the infusion tube provides a measure of confidence to the user that the installed infusion tube and insulin cartridge are free bubbles and leaks. By automatically running the methods for detecting air and leaks described above every time a new insulin cartridge or infusion tube is installed the user gains an increased level of confidence that the system of the insulin cartridge and infusion tube is without air or leak issues. Further, the user can concentrate on other activities while trusting the systems and methods to automatically run detection algorithms and alert the user. In one example, if an air bubble is detected the above described systems and methods for removing an air bubble or adjusting an infusion volume are used to remove or compensate for the bubble. automatically remove the air bubbles as described above. In another example, the user is alerted where there is a leak or air bubble to exchange at least one of the infusion tube and insulin cartridge for a fresh tube or cartridge. Optionally, the user instructs the insulin pump to assess at least one of the insulin cartridge and the infusion tube an as-needed basis according to user instructions (e.g., at discrete times, intervals and the like). In another option, the user instructs the insulin pump to detect the presence of air bubbles or leaks where delivery of insulin is either slow or non-existent.

In another example, the systems and methods for detecting air bubbles and leaks are combined in a single algorithm. For instance, the pump piston is gradually moved forward into the insulin cartridge to a first position to generate a pressure rate of change within the sealed system of the insulin cartridge and the infusion tube. The pump piston is then held at this first position for a period of time. The pump piston is then gradually moved backward toward the starting position. Pressure measurements are taken during each of these steps. By measuring pressure rates of change with the forward and backward movement of the pump piston air bubbles are detected. By measuring pressures over the period of time the pump piston is held at the first position leaks are detected. Combining both detection methods into a single algorithm allows both methods to occur in a single reciprocal cycle of the insulin pump. The combined methods allow for efficient and rapid detection of air bubbles and leaks with only a short delay from normal infusion operations of the insulin pump.

The systems and methods for removing occlusions from the infusion tube allow for continued use of the insulin pump and installed infusion tube after detection of an occlusion. The user is thereby able to continue with current activities while receiving scheduled insulin infusions until a fresh infusion tube is available to exchange with the existing tube (e.g., at home). Further, where an occlusion is detected, the systems and methods are configured to automatically attempt to flush out the occlusion, in one example. Automatic flushing of the occlusion allows the user to continue on with daily activities without needing to monitor and provide instructions to the insulin pump. If the occlusions cannot be flushed by the insulin pump, the user is given an alert that the infusion tube needs to be changed immediately. In another example, the systems and methods are configured to give an alert to the user when an occlusion is detected and request instructions to flush out the occlusion or discontinue attempted insulin infusions until the clogged infusion tube is exchanged for a fresh tube. In still another example, the systems and methods for flushing the occlusion provide an alert when an occlusion is successfully flushed out of the infusion tube providing information to the user about the occlusion and recommending replacement of the infusion tube within a prescribed window of time. Optionally, the systems and methods for removing occlusions perform automatic pressure measurements and alert the use to the presence of the occlusion (e.g., before and after a flushing operation), and facilitate monitoring of the occlusion removal status while the algorithm attempts to remove the occlusion.

Furthermore, by operating the insulin pump at a variety of frequencies and with a variety of forward and backward movement amounts the occlusion experiences a corresponding variety of forces through insulin moving in the infusion tube. The forces are applied in a cyclical fashion and work to dislodge the occlusion and flush it out of the infusion tube.

The systems and methods for removing air bubbles from the insulin cartridge allow for automatic or prompted removal of air bubbles from the cartridge while also filling the infusion tube with the same bubble removing algorithm. As described above, the pump mechanism cycles forward and backward to remove air bubbles. During the cyclical movement, the algorithm instructs the pump to begin gradually increasing forward pump movement (i.e., the direction for infusion) relative to gradually decreasing backward pump movement. Eventually, the backward pump movement ceases, and the forward pump movement fills the infusion tube. This gradual change fills the infusion tube while continuing to move air bubbles out of the insulin cartridge with cyclical pump operation. The insulin pump and filled infusion tube are thereby immediately ready for use after completion of the air bubble removing and infusion tube filling algorithm.

The systems and methods for removing air bubbles from the insulin cartridge operate the cartridge plunger in a cyclical manner with varying amounts of plunger movement and varying frequencies. The frequency of reciprocal movement and the amount of reciprocal movement are changed over the first period to change a variety of flow characteristics within the insulin cartridge (e.g., velocity, pressure, turbulent flow, laminar flow and the like). The changing flow characteristics of the insulin act upon air bubbles within the insulin cartridge to move the air bubbles in the insulin cartridge toward an insulin cartridge opening and into the infusion tubing for eventual discharge through the infusion tubing outlet.

Additionally, the systems and methods for removing air bubbles ensure that as the insulin pump is operated to remove air bubbles before filling of the infusion tube, that forward movement of the pump is less than backward movement. Constraining forward movement of the cartridge plunger ensures that over the first period of the algorithm (the dedicated bubble removing portion of the algorithm) the reciprocating movement of the cartridge plunger does not dispense insulin through the infusion tubing. Insulin is thereby not undesirably dispensed and is instead conserved for later filling operations of the algorithm and intended infusions.

Moreover, in some examples the methods described above for removing air bubbles are performed automatically when an insulin cartridge is installed in the insulin pump. Automatic air bubble removal provides a measure of confidence that an insulin cartridge is without air when insulin infusion begins. Additionally, the user is able to concentrate on other activities while the insulin pump system removes potential air bubbles and fills the infusion tube prior to standard insulin infusing from the pump.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

The invention claimed is:

1. An ambulatory insulin pump, comprising:
   a replaceable insulin cartridge, the insulin cartridge adapted for connection to an infusion set for delivering insulin within the insulin cartridge to a patient;
   a pump mechanism adapted to cooperate with the insulin cartridge to deliver insulin from the insulin cartridge;
   a pressure sensor adapted to be in communication with an internal environment of the insulin cartridge; and
   a controller adapted to operate the pump mechanism to deliver insulin from the insulin cartridge to the patient through the infusion set, the controller further adapted to:
   obtain from the pressure sensor a pressure value of the pressure in the internal environment of the insulin cartridge;
   compare the pressure value to another pressure value, wherein the another pressure value is a pressure value of the pressure in the internal environment of the insulin cartridge previously obtained from the pressure sensor; and
   selectively issue an occlusion alert if the comparison indicates that an occlusion may be present in the infusion set.

2. The ambulatory insulin pump of claim 1, wherein the pressure value is obtained with the pressure sensor after the controller operates the pump mechanism to deliver insulin.

3. The ambulatory insulin pump of claim 2, wherein the pressure value is obtained following linear movement of a portion of the pump mechanism causing insulin to be delivered.

4. The ambulatory insulin pump of claim 1, wherein the occlusion alert includes an instruction to the patient to check the infusion set for an occlusion.

5. The ambulatory insulin pump of claim 1, wherein the occlusion alert is issued if the pressure value is greater than the another pressure value.

6. The ambulatory insulin pump of claim 5, wherein the occlusion alert is only issued if more than one obtained pressure value is greater than the another pressure value.

7. The ambulatory insulin pump of claim 1, wherein the controller is adapted to obtain multiple pressure values of the pressure in the internal environment of the insulin cartridge from the pressure sensor at different times and the occlusion alert is selectively issued based on a comparison relating to the multiple pressure values.

8. The ambulatory insulin pump of claim 1, wherein the controller is further adapted to resume delivery of insulin with the pump mechanism after receiving an indication that an occlusion has been cleared.

9. An ambulatory insulin pump, comprising:
   a replaceable insulin cartridge, the insulin cartridge adapted for connection to an infusion set for delivering insulin within the insulin cartridge to a patient;
   a pump mechanism adapted to cooperate with the insulin cartridge to deliver insulin from the insulin cartridge;
   a pressure sensor adapted to be in communication with an internal environment of the insulin cartridge;
   a pressure detection module adapted to obtain from the pressure sensor a pressure value of the pressure in the internal environment of the insulin cartridge;
   a comparison module adapted to compare the pressure value obtained by the pressure detection module to another pressure value, wherein the another pressure value is a pressure value of the pressure in the internal environment of the insulin cartridge previously obtained from the pressure sensor; and
   an alert module adapted to selectively issue an occlusion alert to the patient if the comparison indicates that an occlusion may be present in the infusion set.

10. The ambulatory insulin pump of claim 9, wherein the pressure value is obtained by the pressure detection module after the pump mechanism is operated to deliver insulin.

11. The ambulatory insulin pump of claim 10, wherein the pressure value is obtained following linear movement of a portion of the pump mechanism causing insulin to be delivered.

12. The ambulatory infusion pump of claim 9, wherein the occlusion alert includes an instruction to the patient to check the infusion set for an occlusion.

13. The ambulatory infusion pump of claim 9, wherein the occlusion alert is issued if the pressure value is greater than the another pressure value.

14. The ambulatory infusion pump of claim 13, wherein the occlusion alert is only issued if more than one obtained pressure value is greater than the another pressure value.

15. The ambulatory infusion pump of claim 9, wherein the pressure detection module is adapted to obtain multiple pressure values of the pressure in the internal environment of the insulin cartridge from the pressure sensor at different times and the comparison module performs a comparison relating to the multiple pressure values.

16. An ambulatory infusion pump device, comprising:
   a replaceable medicament cartridge, the medicament cartridge adapted for connection to an infusion set for delivering medicament within the medicament cartridge to a patient;

a pump mechanism adapted to cooperate with the medicament cartridge to deliver medicament from the medicament cartridge;

a pressure sensor adapted to be in communication with an internal environment of the medicament cartridge; and a controller adapted to operate the pump mechanism to deliver medicament from the medicament cartridge to the patient through the infusion set, the controller further adapted to:

obtain from the pressure sensor a pressure value of the pressure in the internal environment of the medicament cartridge;

compare the pressure value to another pressure value, wherein the another pressure value is a pressure value of the pressure in the internal environment of the medicament cartridge previously obtained from the pressure sensor; and selectively issue an occlusion alert if the comparison indicates that an occlusion may be present in the infusion set.

17. The ambulatory infusion pump device of claim 16, wherein the pressure value is obtained with the pressure sensor after the controller operates the pump mechanism to deliver medicament via linear movement of a portion of the pump mechanism.

\* \* \* \* \*

UNITED STATES PATENT AND TRADEMARK OFFICE
CERTIFICATE OF CORRECTION

PATENT NO. : 9,119,917 B2
APPLICATION NO. : 14/107490
DATED : September 1, 2015
INVENTOR(S) : Blomquist It is certified that error appears in the above-identified patent and that said Letters Patent is hereby corrected as shown below:

In the specification

Column 2, Line 67:
After "in" delete "the".

Column 3, Line 4:
After "in" delete "the".

Column 4, Line 67:
Delete "graduation" and insert -- graduations --.

Column 11, Line 5:
Delete "input for," and insert -- input, for --.

Column 13, Line 38:
After "stand" insert -- - --.

Column 20, Line 15:
Delete "detect" and insert -- detected --.

Column 23, Line 2:
Delete "the and" and insert -- and the --.

Column 23, Line 38:
After "plunger" delete "is".

Column 28, Line 32:
After "ensures" delete "a".

Signed and Sealed this
Ninth Day of February, 2016

Michelle K. Lee
*Director of the United States Patent and Trademark Office*

CERTIFICATE OF CORRECTION (continued)
U.S. Pat. No. 9,119,917 B2

In the specification

Column 32, Line 25:
Delete "increase" and insert -- increased --.

Column 37, Line 37:
After "free" insert -- of --.